US011304704B2

(12) United States Patent
Thomas et al.

(10) Patent No.: US 11,304,704 B2
(45) Date of Patent: Apr. 19, 2022

(54) SURGICAL CLIP APPLIER AND LIGATION CLIPS

(71) Applicant: Covidien LP, Mansfield, MA (US)

(72) Inventors: Justin Thomas, New Haven, CT (US);
Saumya Banerjee, Hamden, CT (US);
Eric Brown, Haddam, CT (US);
Matthew A. Dinino, Newington, CT (US); Gregory R. Morck, Middletown, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 16/433,410

(22) Filed: Jun. 6, 2019

(65) Prior Publication Data

US 2020/0060684 A1 Feb. 27, 2020

Related U.S. Application Data

(60) Provisional application No. 62/721,178, filed on Aug. 22, 2018.

(51) Int. Cl.
*A61B 17/128* (2006.01)
*A61B 17/122* (2006.01)
(Continued)

(52) U.S. Cl.
CPC ...... *A61B 17/1285* (2013.01); *A61B 17/1227* (2013.01); *A61B 17/2909* (2013.01);
(Continued)

(58) Field of Classification Search
CPC .............. A61B 17/122; A61B 17/1227; A61B 17/1285; A61B 17/2909;
(Continued)

(56) References Cited

U.S. PATENT DOCUMENTS

| 3,439,523 A | 4/1969 | Wood |
| 3,713,533 A | 1/1973 | Reimels |

(Continued)

FOREIGN PATENT DOCUMENTS

| BE | 654195 A | 2/1965 |
| CN | 204839635 U | 12/2015 |

(Continued)

OTHER PUBLICATIONS

European Office Action dated Oct. 8, 2020, issued in corresponding EP Appln. No. 19192808, 7 pages.
(Continued)

*Primary Examiner* — Mohamed G Gabr
(74) *Attorney, Agent, or Firm* — Carter, DeLuca & Farrell LLP

(57) ABSTRACT

A clip applier includes an outer tube, an actuation member, and an end effector. The actuation member has a distal portion including a cam member. The end effector includes a first jaw and a second jaw. Each of the first and second jaws includes a proximal portion that defines a cam slot. The cam member of the actuation member is operatively engaged with the cam slots of the first and second jaws such that movement of the actuation member from the first position to the second position causes movement of the end effector from an intermediate position to the open position and subsequently to the clamped position.

13 Claims, 21 Drawing Sheets

(51) Int. Cl.
*A61B 17/29* (2006.01)
*A61B 17/00* (2006.01)

(52) U.S. Cl.
CPC .......... *A61B 2017/0046* (2013.01); *A61B 2017/00367* (2013.01)

(58) Field of Classification Search
CPC .. A61B 2017/00367; A61B 2017/0046; A61B 2017/2936; A61B 2017/2932; A61B 2017/2933; A61B 2017/2939; A61B 2017/2934
See application file for complete search history.

(56) References Cited

U.S. PATENT DOCUMENTS

| | | |
|---|---|---|
| 4,076,120 A | 2/1978 | Carroll et al. |
| 4,146,130 A | 3/1979 | Samuels et al. |
| 4,187,712 A | 2/1980 | Samuels et al. |
| 4,212,303 A | 7/1980 | Nolan |
| 4,212,390 A | 7/1980 | Raczkowski et al. |
| 4,294,355 A | 10/1981 | Jewusiak et al. |
| 4,344,531 A | 8/1982 | Giersch |
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,942,886 A | 7/1990 | Timmons |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,522,830 A | 6/1996 | Aranyi |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,846,255 A | 12/1998 | Casey |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 * | 4/2001 | Levinson .......... A61B 17/1285 606/139 |
| 6,228,097 B1 | 5/2001 | Levinson et al. |
| 6,273,253 B1 | 8/2001 | Forster et al. |
| 6,306,150 B1 | 10/2001 | Levinson |
| 6,349,727 B1 | 2/2002 | Stewart, Jr. |
| 6,391,035 B1 | 5/2002 | Appleby et al. |
| 6,419,682 B1 | 7/2002 | Appleby et al. |
| 6,421,920 B1 | 7/2002 | Jensen |
| 6,439,727 B1 | 8/2002 | Koide |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 2002/0046961 A1 | 4/2002 | Levinson et al. |
| 2002/0177863 A1 | 11/2002 | Mandel et al. |
| 2004/0199178 A1 | 10/2004 | Small |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1 | 7/2009 | Whiting |
| 2011/0224700 A1 | 9/2011 | Schmidt et al. |
| 2011/0295291 A1 | 12/2011 | Trivisani |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0054192 A1 | 2/2014 | Chancibot |
| 2014/0243862 A1 | 8/2014 | Bagaoisan et al. |
| 2014/0276970 A1 | 9/2014 | Messerly et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0209151 A1 | 7/2017 | Brown |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2019/0133590 A1 | 5/2019 | Richard |
| 2019/0159782 A1 | 5/2019 | Kamaraj et al. |
| 2019/0223874 A1 | 7/2019 | Pilletere et al. |
| 2019/0239890 A1 * | 8/2019 | Stokes .......... A61B 34/25 |

FOREIGN PATENT DOCUMENTS

| | | |
|---|---|---|
| CN | 106264647 A | 1/2017 |
| DE | 10116168 A1 | 11/2001 |

(56) References Cited

FOREIGN PATENT DOCUMENTS

| EP | 3524177 A1 | 8/2019 |
|----|------------|--------|
| GB | 2353710 A | 3/2001 |
| WO | 2019089431 A1 | 5/2019 |

OTHER PUBLICATIONS

Chinese International PCT Application No. PCT/CN2018/078294 filed Mar. 7, 2018, Covidien LP.
U.S. Appl. No. 13/972,582, filed Aug. 21, 2013, inventor Manoj Patel.
U.S. Appl. No. 16/261,649, filed Jan. 30, 2019, inventor Justin Thomas, et al.
U.S. Appl. No. 16/261,662, filed Jan. 30, 2019, inventor Justin Thomas et al.
U.S. Appl. No. 16/261,803, filed Jan. 30, 2019, inventor, Justin Thomas, et al.
U.S. Appl. No. 16/364,648, filed Mar. 26, 2019, inventor, Roy J. Pilletere, et al.
U.S. Appl. No. 16/432,984, filed Jun. 6, 2019, inventor, Justin Thomas, et al.
European Search Report dated Nov. 12, 2019, issued in EP Appln. No. 19192808, 9 pages.

\* cited by examiner

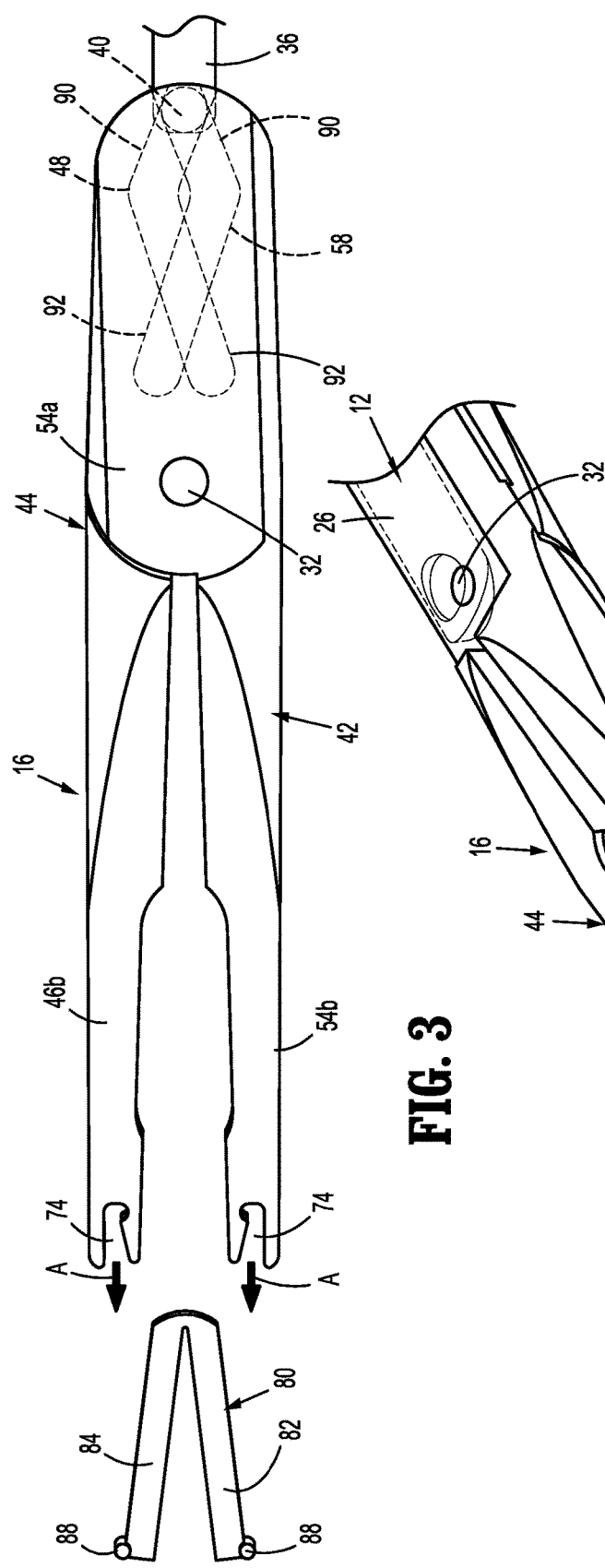
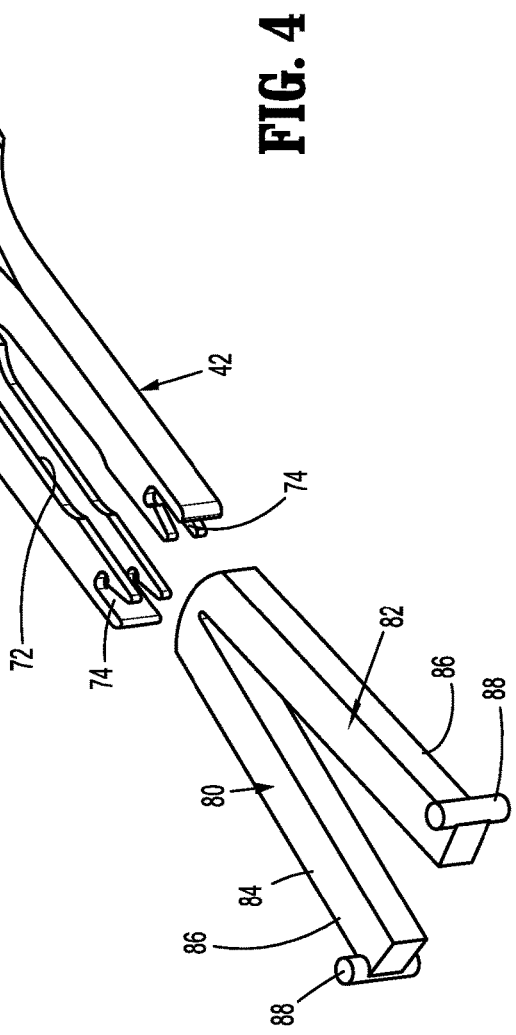

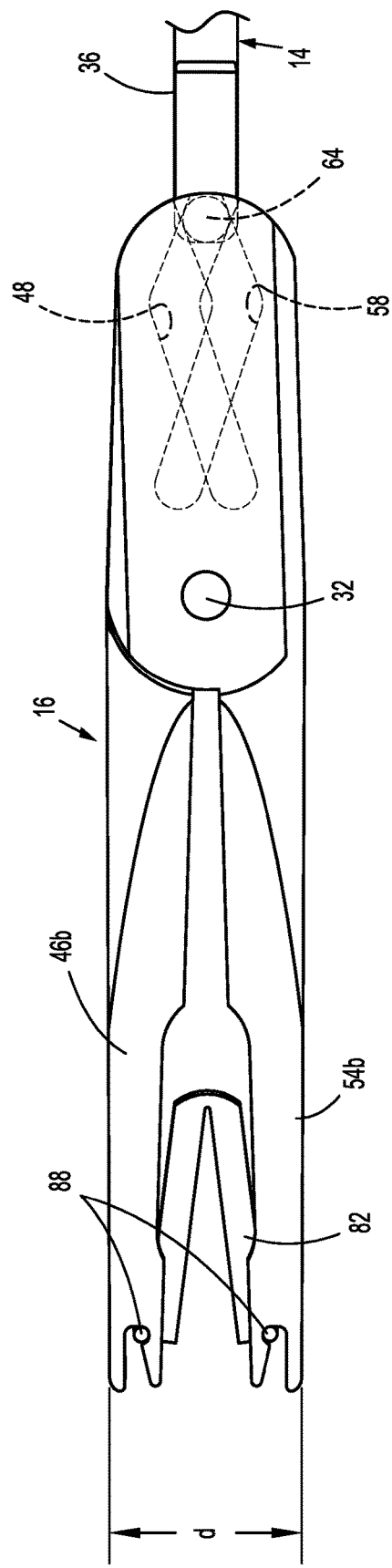
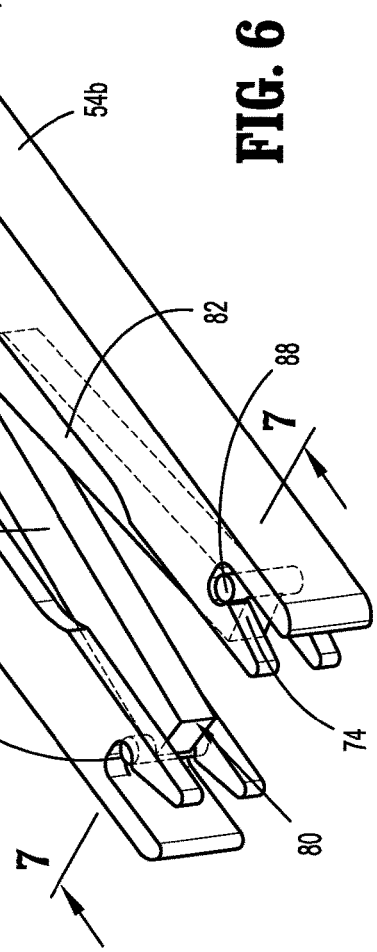

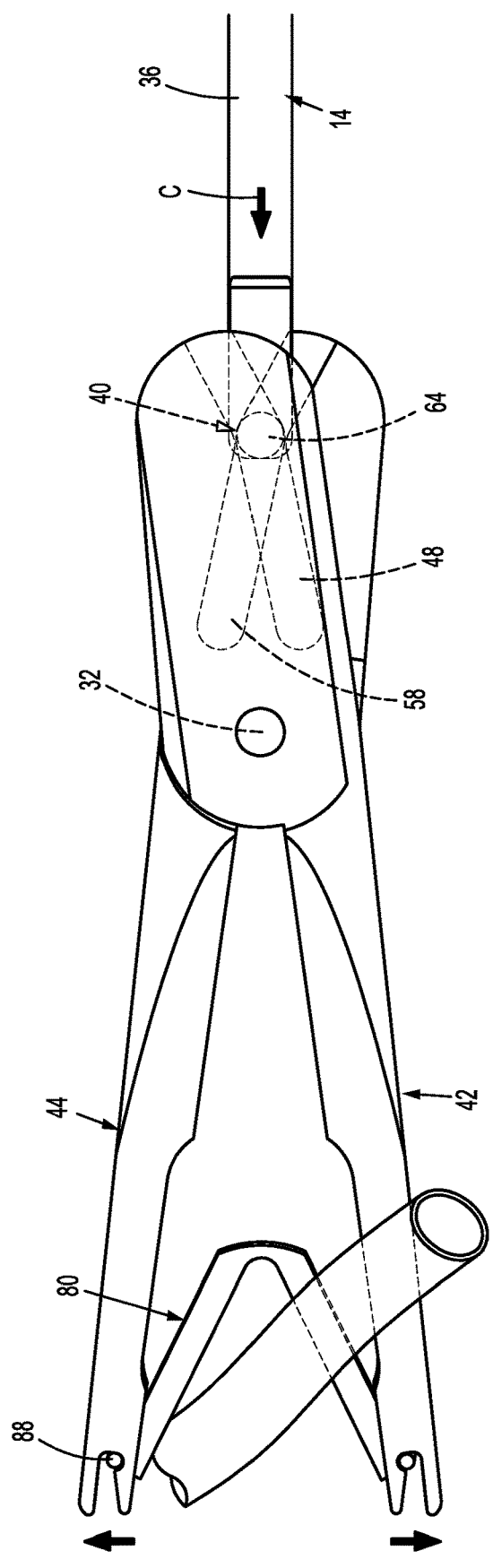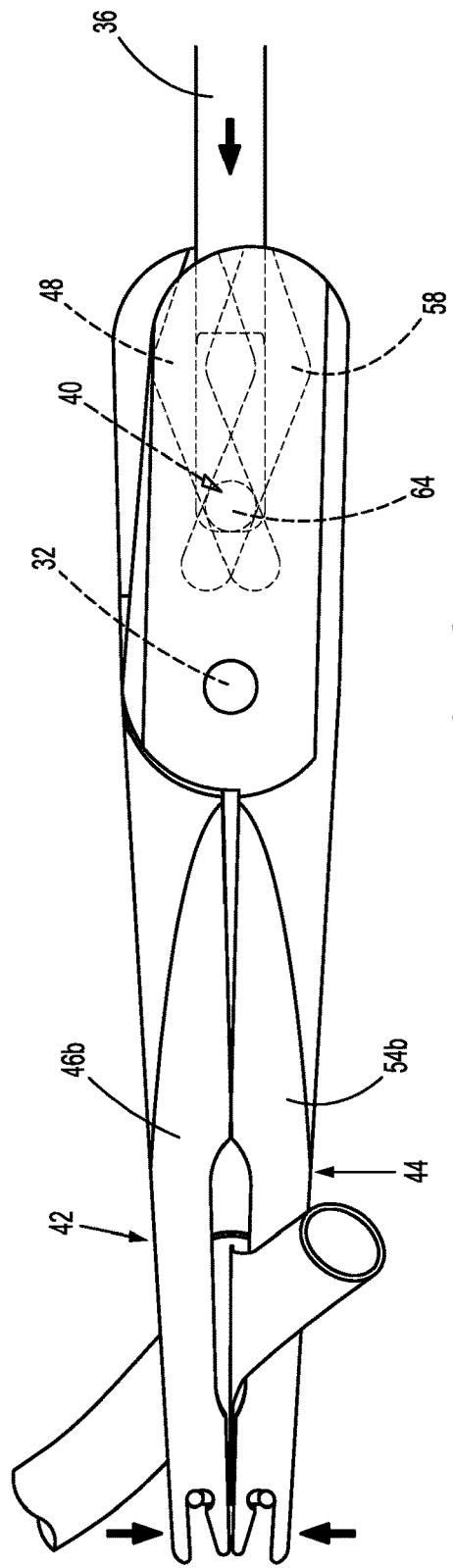
FIG. 9
FIG. 10

SURGICAL CLIP APPLIER AND LIGATION CLIPS

CROSS-REFERENCE TO RELATED APPLICATION

This application claims the benefit of and priority to U.S. Provisional Patent Application No. 62/721,178 filed Aug. 22, 2018, the entire disclosure of which is incorporated by reference herein.

BACKGROUND

1. Technical Description

The present disclosure is directed to a surgical clip applier and, more particularly, to a surgical clip applier that includes an actuator that is movable in one direction to initially open jaws of a ligation clip and subsequently close the jaws of the ligation clip. The present disclosure is also directed various embodiments of ligation clips including tissue retaining structure.

2. Background of Related Art

Surgical clip appliers for placing a ligation clip onto tissue during surgical procedures to ligate the tissue are well known in the art. The surgical clip appliers are configured for use during both open surgical procedures and minimally invasive surgical procedures. Typically, during a minimally invasive surgical procedure, after a ligation clip has been loaded into the clip applier, the clinician must move an actuator of the clip applier in a first direction to partially close ("pre-close") the clip in order to insert the clip applier and ligation clip through a trocar assembly. Thereafter, the clinician must move the actuator in an opposite direction to open the ligation clip for placement about tissue. The initial step pre-closing the ligation clip may cause the ligation clip to fall out of the jaws of the clip applier when the clip applier is advanced through the trocar assembly if the ligation clip is not fully secured to the jaws of the clip applier. In addition, if the ligation clip is pre-closed to a greater extent than necessary, the ligation clip may become deformed or latch prematurely.

A continuing need exists in the art for a minimally invasive clip applier that can position a ligation clip through a trocar assembly and open the ligation clip to position about tissue while obviating existing problems described above.

SUMMARY

One aspect of the present disclosure is directed to a clip applier including an outer tube, an actuation member, and an end effector. The outer tube defines a longitudinal axis and a longitudinal bore that extends along the longitudinal axis. The actuation member has a proximal portion and a distal portion including a cam member, wherein the actuation member is movable within the longitudinal bore of the outer tube between first and second positions. The end effector includes a first jaw and a second jaw. Each of the first and second jaws is pivotably coupled to the outer tube such that the end effector is movable between open and clamped positions. Each of the first and second jaws includes a proximal portion that defines a cam slot, wherein the cam member of the actuation member is operatively engaged with the cam slots of the first and second jaws such that movement of the actuation member from the first position to the second position causes movement of the end effector from an intermediate position to the open position and subsequently to the clamped position.

In embodiments, the cam member includes a first protrusion that is received in the cam slot of the first jaw and a second protrusion that is received in the cam slot of the second jaw.

In some embodiments, the cam slots include a proximal portion that extends outwardly away from the longitudinal axis of the outer tube and a distal portion that extends towards the longitudinal axis of the outer tube.

In certain embodiments, the outer tube includes a distal portion defining a clevis, wherein the first and second jaws are pivotably secured to the clevis by a pivot member.

In embodiments, the distance between an outer surface of the first and second jaws when the end effector is in the intermediate position is no greater than the diameter of the outer tube.

In some embodiments, each of the first and second jaws defines a channel and a cutout, wherein the channel of each of the first and second jaws is dimensioned to receive a leg of a ligation clip and the cutout of each of the first and second jaws is configured to receive a boss of the ligation clip.

Another aspect of the present disclosure is directed to a method of clamping a ligation clip onto tissue that includes positioning a ligation clip between first and second jaws of an end effector of a clip applier with the end effector in an intermediate position located between an open position and a clamped position; and moving an actuation member in a first direction to initially move the first and second jaws of the end effector from the intermediate position to the open position and to subsequently move the end effector from the open position through the intermediate position to the clamped position.

In embodiments, the method includes introducing the end effector into a body cavity through a trocar assembly with the end effector in the intermediate position.

In some embodiments, positioning the ligation clip on the end effector includes sliding first and second legs of the ligation clip into slots in the first and second jaws of the end effector to position bosses on the first and second legs of the ligation clip within cutouts formed in the first and second jaws of the end effector of the clip applier.

In certain embodiments, the method includes moving the actuation member to move the end effector to the open position.

In embodiments, the method includes manipulating the clip applier to position the first and second legs of the ligation clip about a body vessel when the end effector is in the open position.

In some embodiments, the method includes moving the actuator to move the end effector from the open position through the intermediate position and to the clamped position to clamp the ligation clip about the body vessel.

In certain embodiments, moving the actuation member includes advancing the actuation member.

In embodiments, the method includes withdrawing the end effector from the trocar assembly after the end effector is moved to the clamped position.

BRIEF DESCRIPTION OF THE DRAWINGS

Various embodiments of the presently disclosed clip applier are described herein below with reference to the drawings, wherein:

FIG. 3 is a top view of a distal portion of the clip applier shown in FIG. 1 as the distal portion of the clip applier is advanced toward a ligation clip;

FIG. 4 is a side perspective view of the distal portion of the clip applier and the ligation clip shown in FIG. 3;

FIG. 5 is a top view of the distal portion of the clip applier and the ligation clip shown in FIG. 3 with the ligation clip supported on jaws of the clip applier;

FIG. 6 is an enlarged view of the indicated area of detail shown in FIG. 1;

FIG. 9 is a top view of the clip applier and ligation clip shown in FIG. 8 with the clip applier and ligation clip moved to open positions about body tissue;

FIG. 10 is a top view of the clip applier and ligation clip shown in FIG. 9 with the clip applier and ligation clip clamped about the body tissue;

DETAILED DESCRIPTION OF EMBODIMENTS

Figure 1:
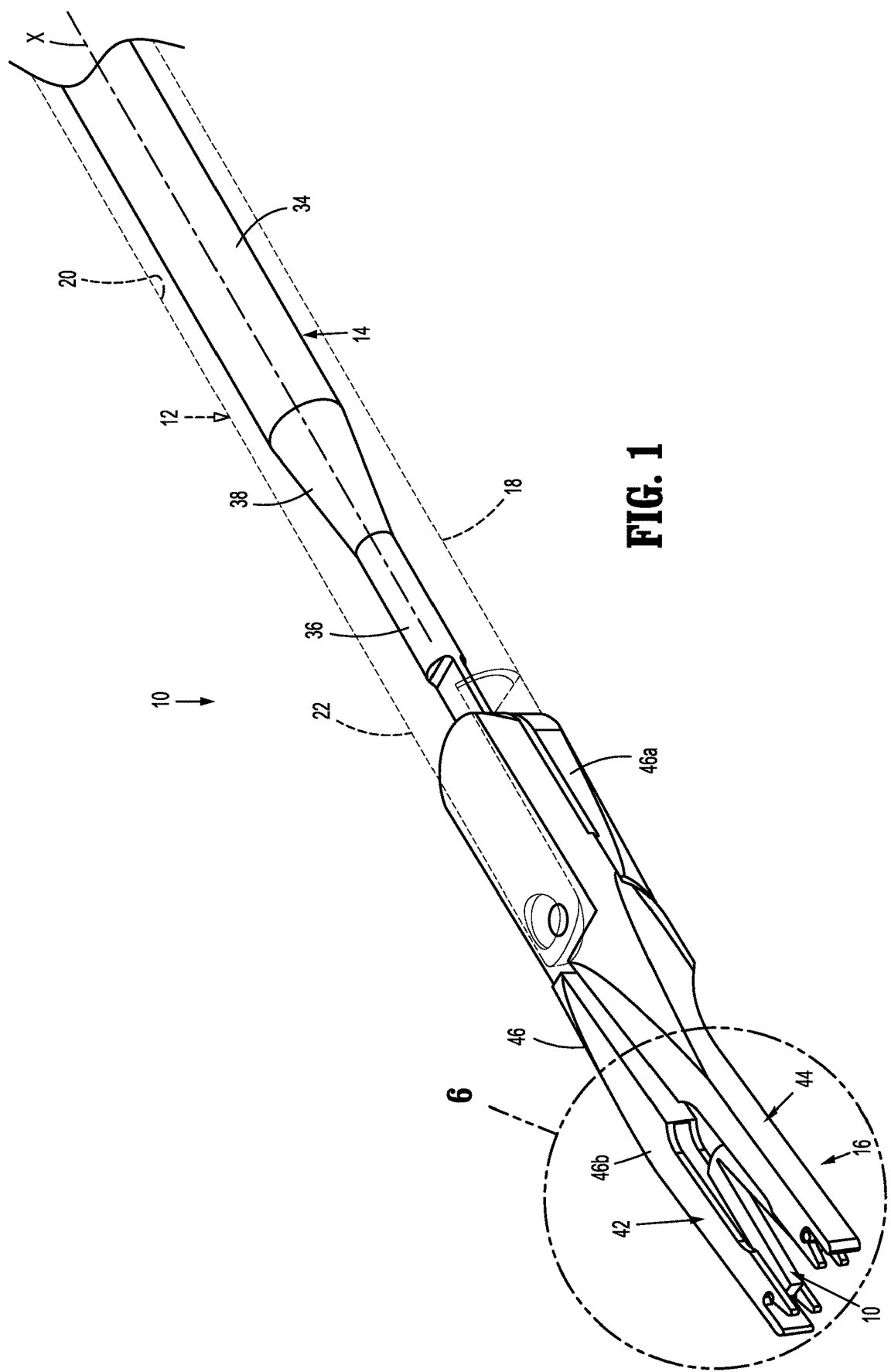
FIG. 1 is a perspective view from above of an exemplary embodiment of the presently disclosed clip applier in a pre-actuated position with an outer tube shown in phantom.

The presently disclosed surgical clip applier and ligation clips will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
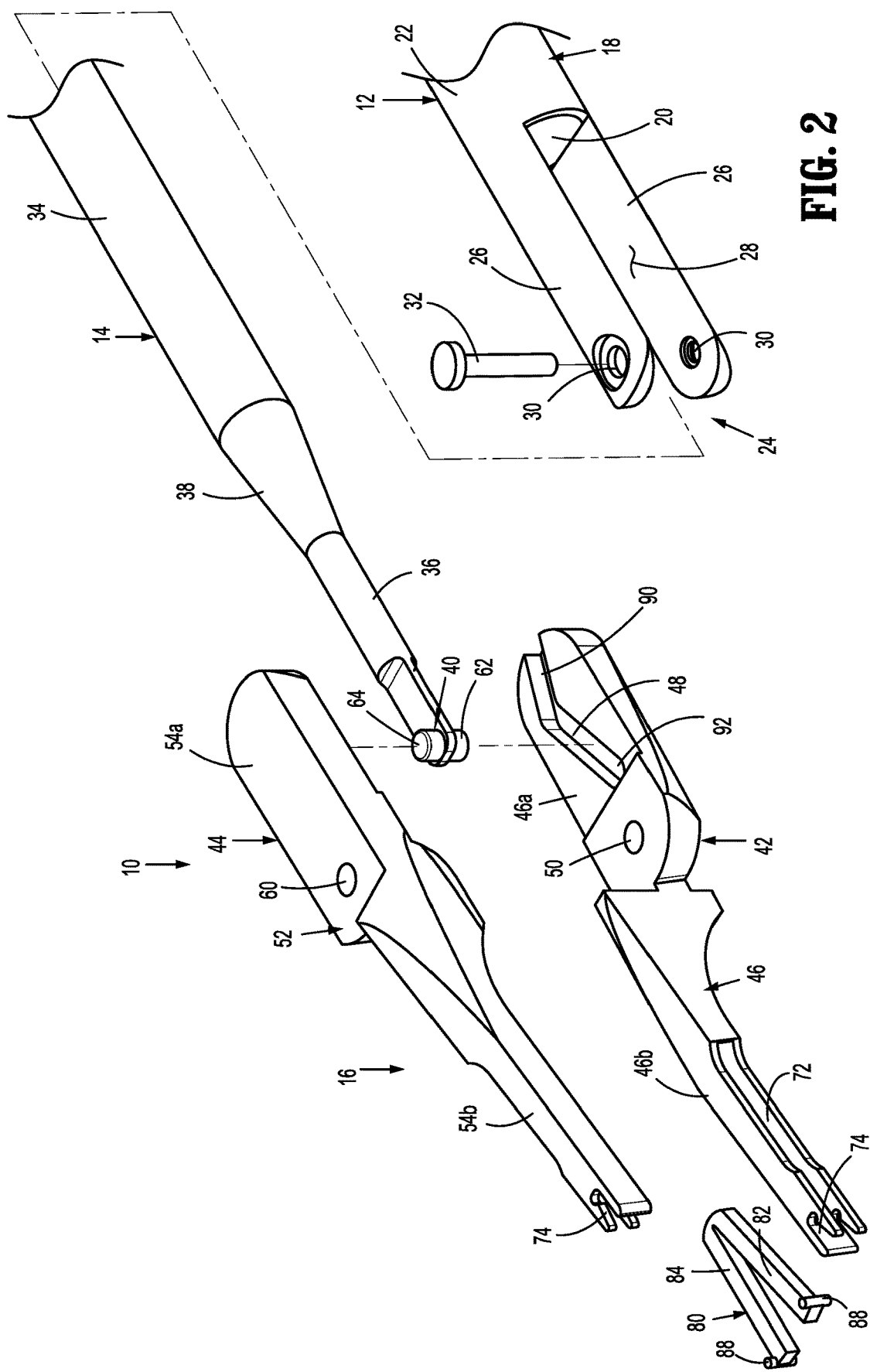
FIG. 2 is an exploded view of the clip applier shown in FIG. 1 with the outer partially cut away.
Figure 7:
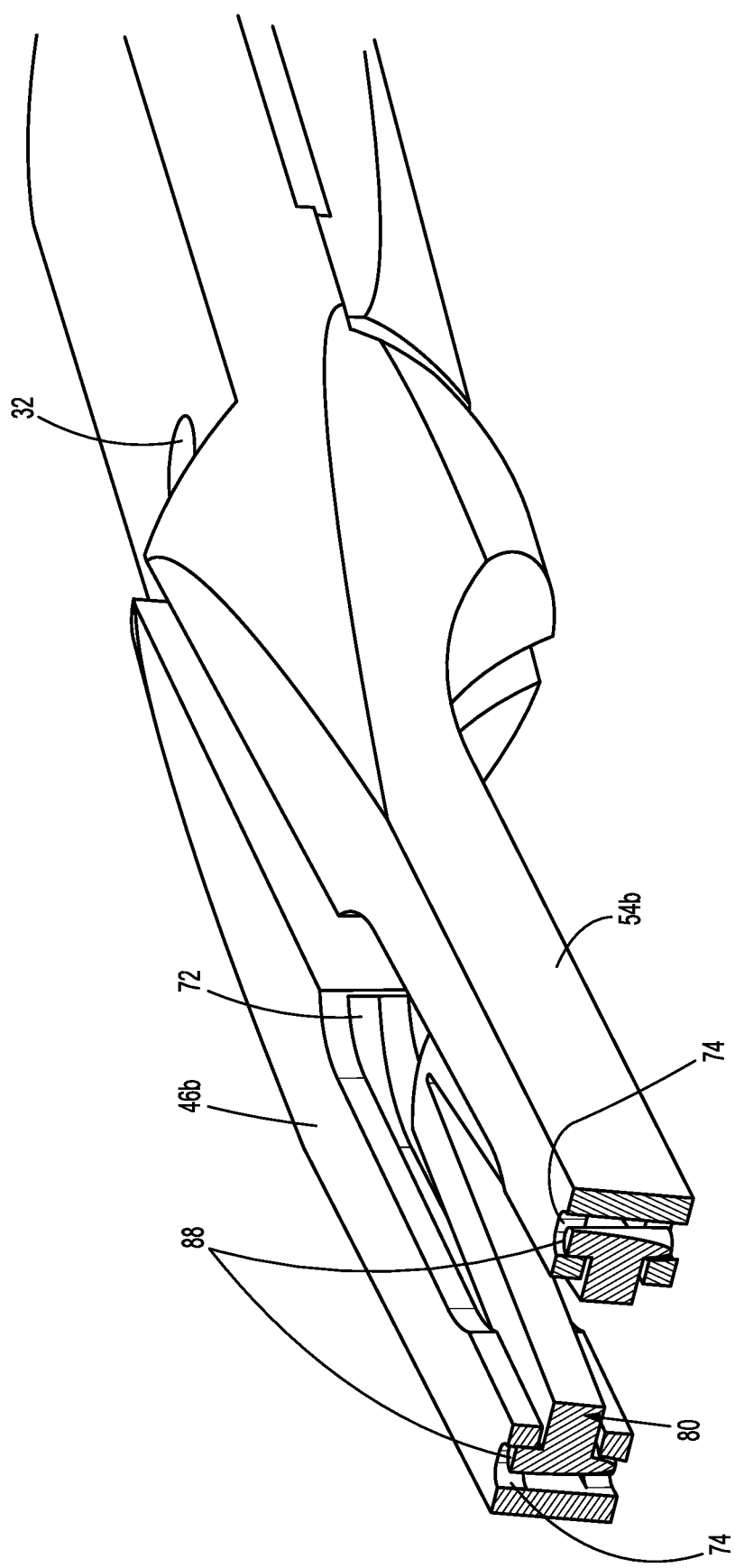
FIG. 7 is a cross-sectional view taken along section line 7-7 of FIG. 6.

Referring to FIGS. 1-3, the presently disclosed surgical clip applier is shown generally as clip applier 10. Clip applier 10 includes an outer tube 12 (FIG. 2) defining a longitudinal axis "X" (FIG. 1), an actuation member 14, and an end effector 16. The outer tube 12 includes a hollow body 18 that defines a longitudinal bore 20 (FIG. 2) and has a proximal end (not shown) and a distal end 22. The distal end 22 of the hollow body 18 forms a clevis 24 that has spaced arms 26 that define a recess 28. Each of the arms 26 has a distal end that defines a transverse bore 30 that is dimensioned to receive a pivot member 32.

The actuation member 14 is received within the longitudinal bore 20 (FIG. 2) of the outer tube 12 and is movable between a retracted position and an advanced position in relation to the outer tube 12 to operate the end effector 16 as described in detail below. In embodiments, the actuation member 14 has a proximal portion 34 having a first diameter, a distal portion 36 having a second diameter that is smaller than the first diameter, and a tapered portion 38 that interconnects the proximal portion 34 of the actuation member 34 to the distal portion 36 of the actuation member 14. Alternately, other actuation member 14 configurations are envisioned. The distal portion 36 includes a cam member 40 that is operatively engaged with the end effector 16 to control operation of the end effector 16 as described below.

The end effector 16 includes a first jaw 42 and a second jaw 44. The first jaw 42 includes a body 46 having a proximal portion 46a and a distal portion 46b. The proximal portion 46a of the body 46 of the first jaw 42 defines a cam slot 48 (FIG. 3) and a bore 50. Similarly, the second jaw 44 includes a body 52 having a proximal portion 54a and a distal portion 54b. The proximal portion 54a of the body 52 of the second jaw 44 defines a cam slot 58 (FIG. 3) and a bore 60. The cam slots 48, 58 of the first and second jaws 42, 44, respectively, are engaged with the distal portion 36 of the actuation member 14 as described in further detail below to translate movement of the actuation member 14 to movement of the first and second jaws 42, 44. The bores 50, 60 of the first and second jaws 42, 44, respectively, receive the pivot member 32 to pivotably secure the first and second jaws 42, 44 to the clevis 24 of the outer tube 12 such that the jaws 42, 44 are pivotable in relation to each other between an open position (FIG. 9) and a clamped position (FIG. 10.) Each of the distal portions 46b, 54b of the first and second jaws 42, 44, respectively, define a slot 72 (FIG. 4) and a distal cutout 74.

Figure 11:
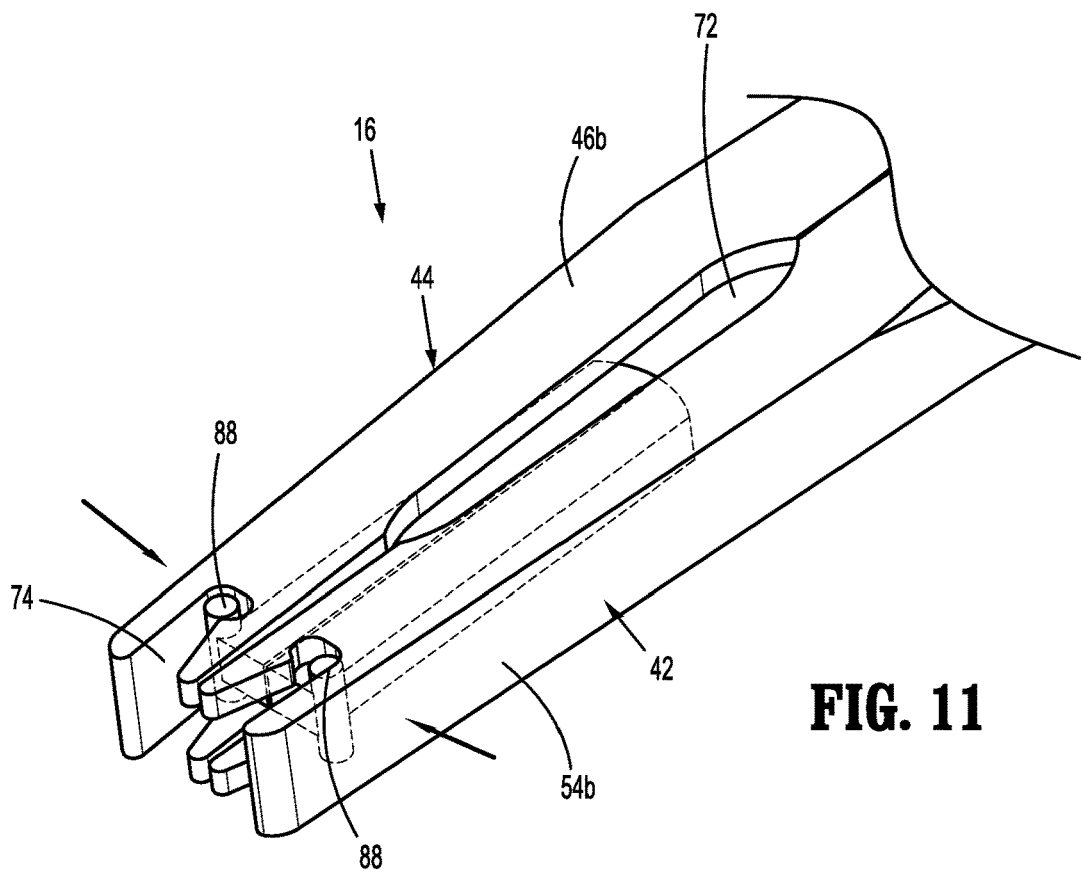
FIG. 11 is a side, perspective view from the distal end of the jaws of the clip applier and the ligation clip in a clamped position.

Referring also to FIGS. 4-7, in embodiments, the cam member 40 of the distal portion 36 of the actuation member 14 includes a first protrusion 62 and a second protrusion 64 (FIG. 2). The first protrusion 62 is received within the cam slot 48 of the first jaw 42 and the second protrusion 64 is received within the cam slot 58 of the second jaw 44. The first and second jaws 42, 44 are rotatably secured to the clevis 24 of the outer tube 12 by the pivot member 32. When the actuation member 14 is in a fully retracted position, the first and second protrusions 62, 64 of the cam member 40 are received in a proximal end of the cam slots 48, 58 of the first and second jaws 42, 44, respectively. In this position, the first and second jaws 42, 44 are retained in an intermediate position (FIG. 5) between an open position (FIG. 9) and a clamped position (FIG. 11.) In the intermediate position, the jaws 42, 44 are positioned to be received through a trocar assembly 70 (FIG. 8), e.g., a 5 mm or 10 mm trocar assembly.

The end effector 16 of the clip applier 10 is configured to support a ligation clip 80 having first and second legs 82, 84 (FIG. 4). The first and second legs 82, 84 are coupled to each other such that the first leg 82 is pivotable in relation to the second leg 84 between an open position (FIG. 9) and a clamped position (FIG. 10.) Each of the first and second legs 82, 84 of the ligation clip 80 includes a body 86 (FIG. 4) and a boss 88 that extends outwardly of the body 86.

The slots 72 and the cutouts 74 of the first and second jaws 42, 44 of the end effector 16 are dimensioned to receive and support the ligation clip 80. More specifically, each of the legs 82, 84 of the ligation clip 80 are received within a slot 72 of one of the first and second jaws 42, 44 and each of the bosses 88 of the ligation clip 80 are received within a cutout 74 of one of the jaws 42, 44. The bosses 88 of the legs 82, 84 of the ligation clip 80 prevent the ligation clip from becoming disengaged from the jaws 42, 44 of the end effector 16 in any direction except through the distal end of the slots 72 and cutouts 74 of the first and second jaws 42, 44, i.e., the bosses 88 prevent lateral movement of the ligation clip 80 within the jaws 42, 44 of the clip applier 10.

A ligation clip 80 can be loaded onto the end effector 16 of the clip applier 10 by advancing the end effector 16 in relation the ligation clip 80 in the direction indicated by arrows "A" in FIG. 3 such that the first and second legs 82, 84 of the ligation clip 80 are received within the slots 72 of the first and second jaws 42, 44. The end effector 16 is moved in the direction indicated by arrows "A" in relation to the ligation clip 80 until the bosses 88 are received within the cutouts 74 (FIG. 5) of the first and second jaws 42, 44. The ligation clip 80 should be loaded onto the end effector 16 of the clip applier 10 when the actuation member 14 in the retracted position such that the cam member 40 is located in the proximal end of the cam slots 48, 58 of the first and second jaws 42, 44, respectively. When the actuation member 14 is in the retracted position and the cam member 40 is located in the proximal end of the cam slots 48, 58, the end effector 16 is in the intermediate position (FIGS. 5 and 6) located between the open and clamped positions. In the intermediate position, the distance "d" (FIG. 5) between the outer surfaces of the first and second jaws 42, 44 is substantially equal to the outer diameter of the outer tube 12 of the clip applier 10. This allows the end effector 16 to be received in small diameter trocar assembly 70 (FIG. 8.)

Figure 8:
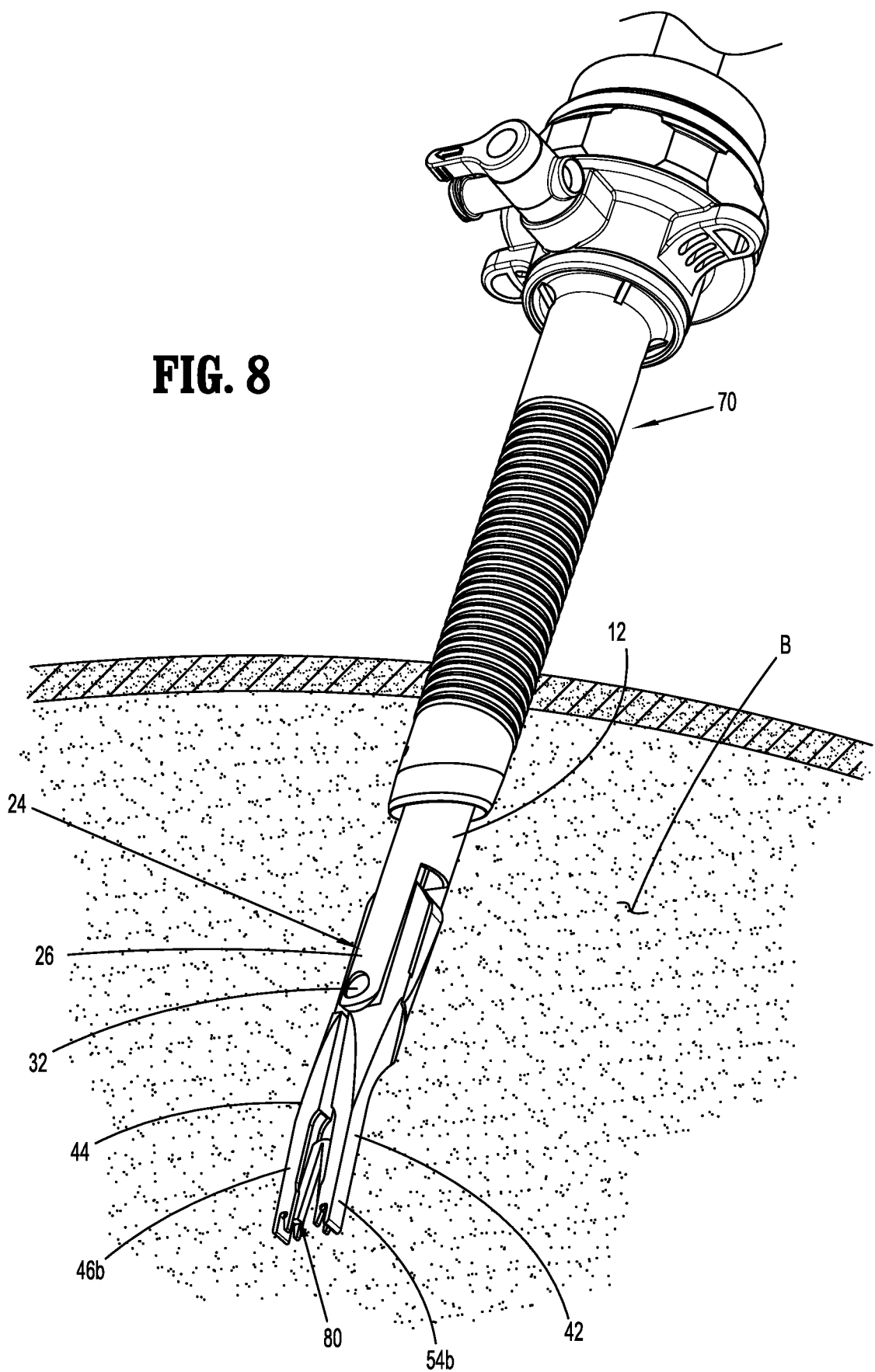
FIG. 8 is a side perspective view of the clip applier and ligation clip shown in FIG. 1 with the clip applier positioned through a trocar assembly into a body cavity in the pre-actuated position.

Referring to FIGS. 8 and 9, after the distal portion of the clip applier 10 including the end effector 16 is inserted through the trocar assembly 70 into a body cavity "B" of a patient with the end effector 16 in the intermediate position, the actuation member 14 can be advanced distally in the direction indicated by arrow "C" in FIG. 9 within the outer tube 12 to advance the cam member 40 within the cam slots 48, 58 of the first and second jaws 42, 44. The cam slots 48, 58 are configured such that during initial advancement of the cam member 40 within a proximal portion 90 of the cam slots 48, 58, the cam member 40 urges the jaws 42, 44 of the end effector 16 outwardly from each other to move the end effector 16 to the open position (FIG. 9) and during further advancement of the cam member 40 within a distal portion 92 of the cam slots 48, 58, the cam member 40 urges the jaws 42, 44 of the end effector 16 inwardly towards each other to move the end effector 16 to the clamped position (FIG. 10.) In embodiments, the cam slots 48, 58 have a boomerang shape with the proximal portion of the cam slots 48, 58 extending outwardly from the longitudinal axis "X" (FIG. 1) and the distal portion of the cam slots 48, 58 extending back towards and across the longitudinal axis "X" defined by the outer tube 12 of the clip applier 10.

Figure 12:
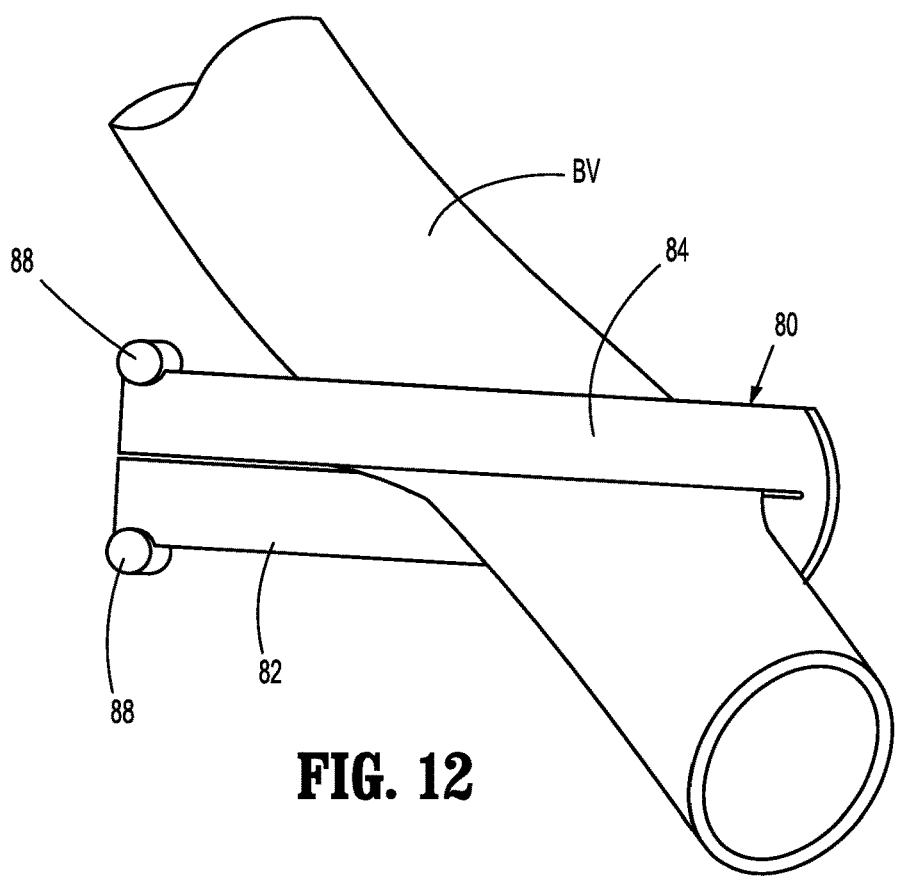
FIG. 12 is a side perspective view of the ligation clip shown in FIG. 11 clamped about the body tissue.

Referring to FIGS. 11 and 12, when the actuation member 14 is advanced within the outer tube 12 (FIG. 2) to move the cam member 40 within the distal portion 92 (FIG. 3) of the cam slots 48, 58 of the first and second jaws 42, 44, the jaws 42, 44 are moved to the clamped position to compress the ligation clip 80 and move the ligation clip 80 to the clamped position about body tissue, e.g., a body vessel "BV" (FIG. 12).

The presently disclosed clip applier 10 includes an actuation member 14 that is initially positioned in a fully retracted position to position the end effector 16 in a partially closed or intermediate position to facilitate passage of the end effector 16 through a small diameter trocar assembly 70. The actuation member 14 is movable in a single direction to initially move the jaws 42, 44 of the end effector 16 to an open position (FIG. 9) to facilitate positioning of the ligation clip 80 about tissue and subsequently to the clamped position (FIG. 11) to ligate tissue "BV". After the ligation clip 80 is clamped about the body vessel "BV", the clip applier 10 can be withdrawn from the trocar assembly 70.

FIGS. 13-20 illustrate an exemplary embodiment of a ligation clip that is suitable for application with the clip applier 10 (FIG. 1) shown generally as ligation clip 100. The ligation clip 100 defines a longitudinal axis "Z" (FIG. 15) and includes a first leg 112, a second leg 114, and a hinge portion 116 coupling the first leg 112 to the second leg 114.

Figure 15:
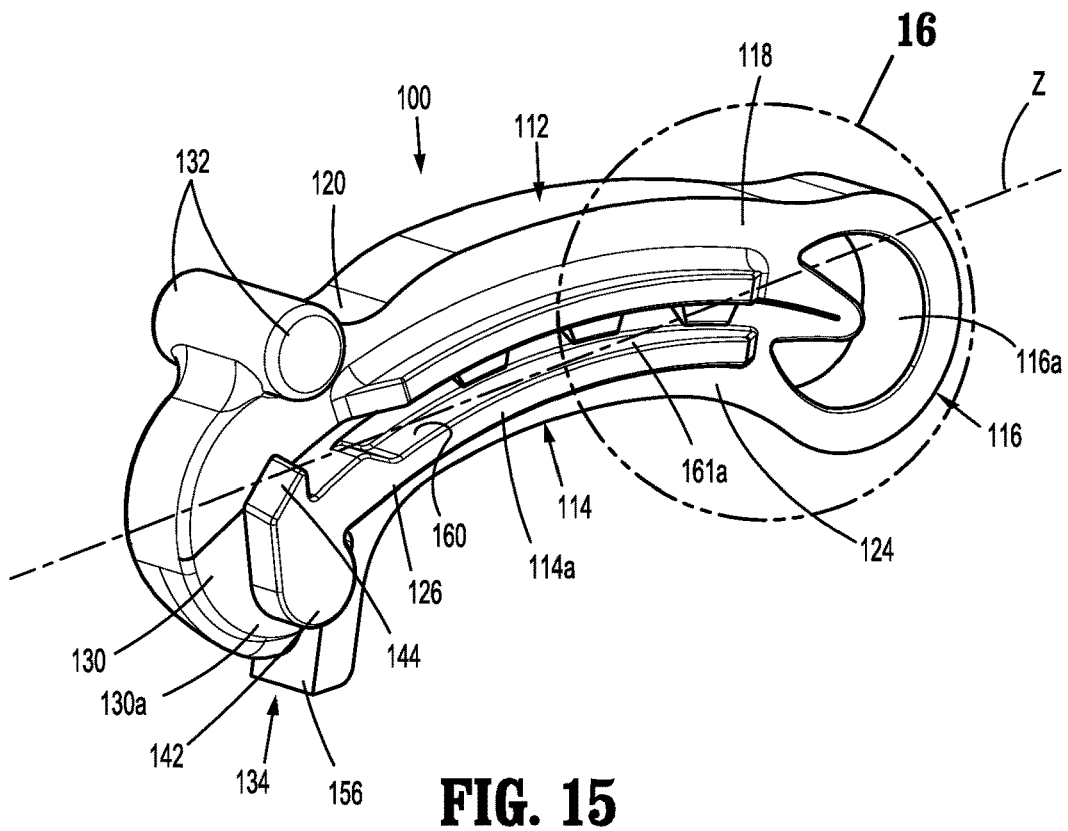
FIG. 15 is a side perspective view of the ligation clip shown in FIG. 13 in a clamped position.
Figure 16:
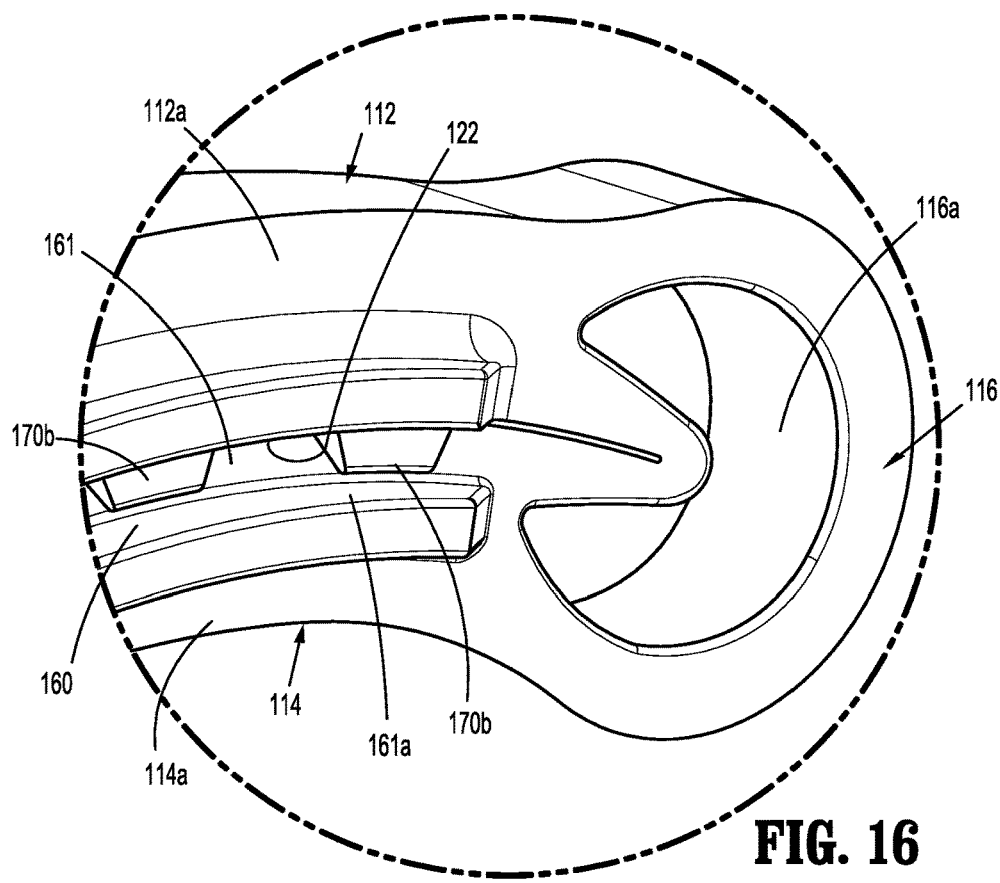
FIG. 16 is an enlarged view of the indicated area of detail shown in FIG. 15.

The first leg 112 is pivotable in relation to the second leg 114 about the hinge portion 116 to move the ligation clip 100 between an open position (FIG. 13) and a clamped position (FIG. 15). In embodiments, the first and second jaws 112, 114 are curved along the longitudinal axis "Z" (FIG. 15) although other leg configurations are envisioned. In embodiments, the hinge portion 116 may be integrally formed with the first and second jaws 112, 114, e.g., a living hinge, and may define a crescent shaped through bore 116a to facilitate movement of the first leg 112 in relation to the second leg 114 between the open and clamped positions. The through bore 116a also allows for substantially complete closure of the proximal portions of the first and second jaws 112, 114.

Figure 13:
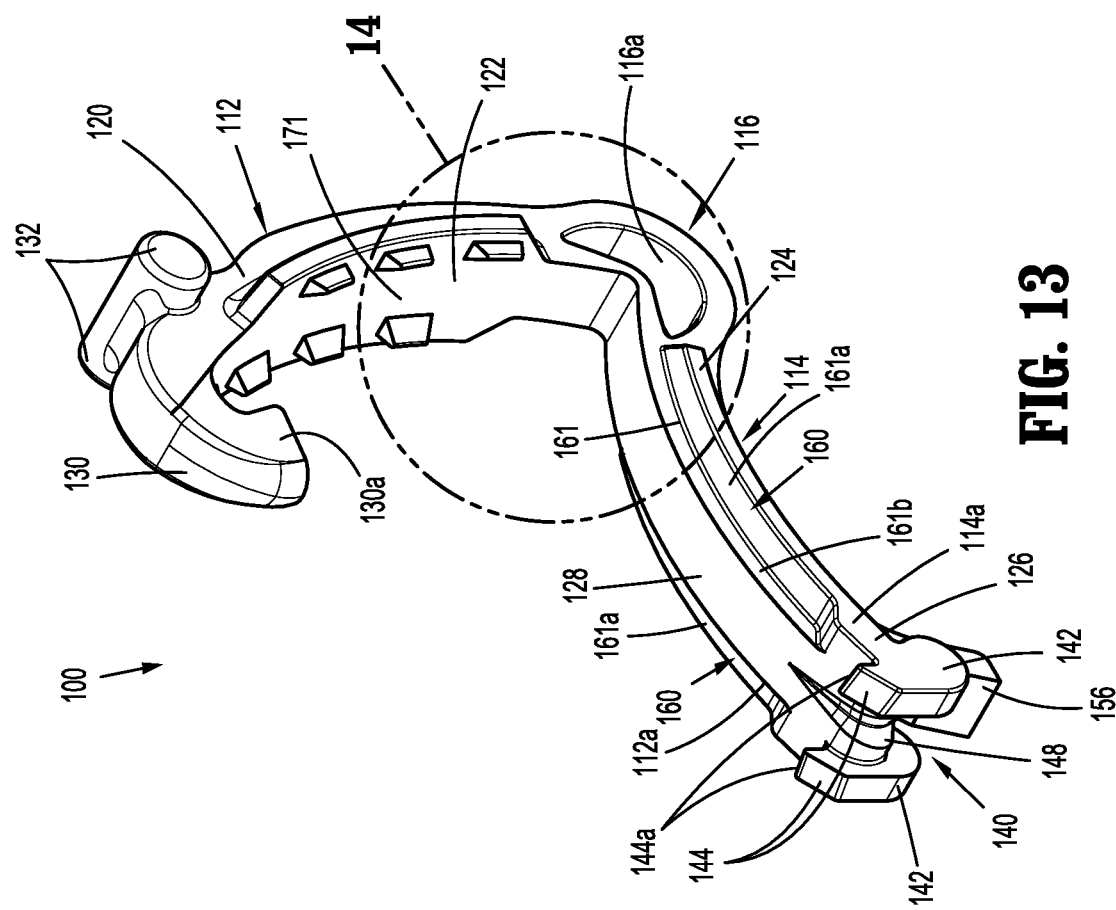
FIG. 13 is a side perspective view of an exemplary embodiment of a presently disclosed ligation clip in an open position.
Figure 14:
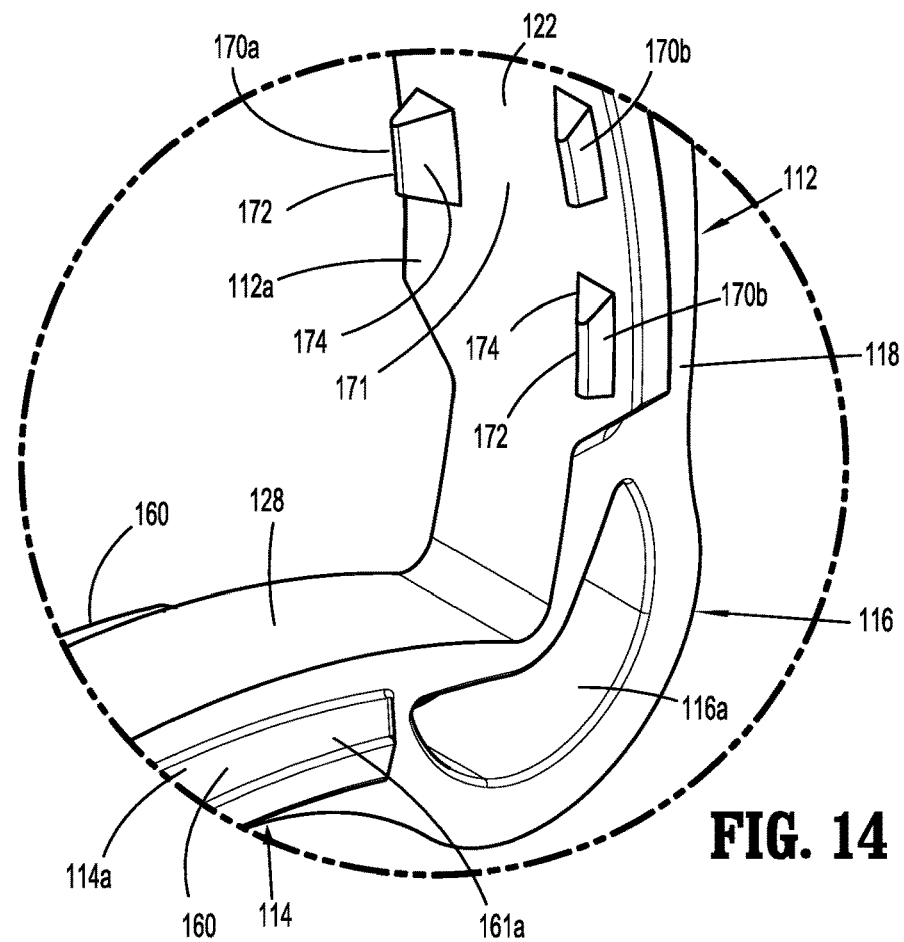
FIG. 14 is an enlarged view of the indicated area of detail shown in FIG. 13.

The first leg 112 has a body 112a having a proximal portion 118, a distal portion 120, and a clamping surface 122 (FIG. 14). The second leg 114 has a body 114a having a proximal portion 124, a distal portion 126, and a clamping surface 128 (FIG. 13). The proximal portions 118, 124 of the first and second jaws 112, 114, respectively, are coupled to the hinge portion 116 such that the ligation clip 100 is pivotable between the open position (FIG. 13) and the clamped position (FIG. 15). The distal portion 120 of the first leg 112 includes a first locking element 130 and spaced transverse bosses 132. The first locking element 130 includes a hooked portion 130a that extends downwardly and proximally from the clamping surface 122 to define a portion of a latching mechanism 134 (FIG. 15) that is configured to retain the ligation clip 100 in a clamped position as described in further detail below.

In embodiments, the bosses 132 are cylindrical and may form part of a single member supported on the distal portion 120 of the first leg 112. The bosses 132 are configured to be received within the cutouts 74 (FIG. 3) of a clip applier 10 (FIG. 1) to support the ligation clip 100 on the clip applier 10.

The distal portion 126 of the second leg 114 includes a second locking element 140 (FIG. 13), spaced bosses 142, and spaced teeth 144. The spaced teeth 144 are configured to engage and/or penetrate tissue. In embodiments, the teeth 144 have an apex or pointed end 144a that grips and stretches tissue as the ligation clip 100 is moved from the open position (FIG. 13) towards the clamped position (FIG. 15) to improve the ligating characteristics of the ligation clip 100. The second locking element 140 FIG. 13 defines an engagement surface 146 (FIG. 17) and a cam surface 148 (FIG. 13). The cam surface 148 and the engagement surface 146 are configured to receive and guide the first locking element 130 into locking engagement with the second locking element 140 when the ligation clip 100 is moved to the clamped position (FIG. 15) to secure the ligation clip 100 in the clamped position. In particular, the cam surface 148 (FIG. 13) is configured to deflect the first locking element 130 outwardly in a distal direction as the first locking element 130 passes over the cam surface 148 of the second locking element 140 such that when the first locking element 130 moves past the cam surface 148, the first locking element 130 resiliently moves into engagement with the second locking element 140 (FIG. 15).

The bosses 142 of the second leg 114 are similar to the bosses 132 of the first leg 112. More specifically, the bosses 142 extend outwardly from the body 114a of the second leg 114 and are configured to be received within the cutouts 74 (FIG. 3) of the jaws 42, 44 of the clip applier 10 to support the ligation clip 100 on the clip applier 10.

In embodiments, the second leg 114 includes a spring arm 156 that is positioned to engage the first locking element 130 when the ligation element 100 is moved to the clamped position to retain the first locking element 130 and the second element 140 in the latched position (FIG. 15). The spring arm 156 is positioned to engage and be deflected by the first locking element 130 to create a compressive force within the spring arm 156 that presses the first locking element 130 into engagement with the second locking element 140 when the ligation clip 100 is in the clamped position (FIG. 15).

The second clamping surface 128 of the second leg 114 is substantially flat and is positioned between a pair of longitudinal recesses 160 (FIG. 13) that extend along opposite sides of the second clamping surface 124. The second clamping surface 128 is in opposition with the first clamping surface 122 of the first leg 114 when the ligation clip 100 is in the clamped position (FIG. 15). In embodiments, the longitudinal recesses 160 may have a rectangular configuration and be defined by a substantially flat base wall 161a and a side wall 161b. Other recess configurations are envisioned. In some embodiments, the longitudinal recesses 160 extend substantially the entire length of the second tissue clamping surface 128. Alternately, it is envisioned that the longitudinal recesses 160 may include a plurality of recess sections that are longitudinally spaced from each other and extend over a length less than the entire length of the second tissue clamping surface 128.

The first clamping surface 122 is substantially flat and supports a first row of protrusions 170a and a second row of protrusions 170b. Each of the rows of protrusions 170a, 170b is axially aligned with one of the longitudinal recesses 160. Each of the protrusions 170a of the first row of protrusions 170a is spaced from but longitudinally aligned with each of the other protrusions 170a in the first row of protrusions 170a along a first side of the first clamping surface 122. Similarly, each of the protrusions 170b of the second row of protrusions 170b is longitudinally aligned with each of the other protrusions 170b in the second row of protrusions 170b along a second side of the first clamping surface 122 opposite to the first side of the first clamping surface 122. The protrusions 170a, 170b are spaced transversely from each other to define an unobstructed central channel 171 (FIG. 14) between the first and second rows of protrusions 170a, 170b on the first clamping surface 122. The central channel 171 receives the second clamping surface 128 of the second leg 114 when the ligation clip 100 is in the clamped position (FIG. 15.) In the clamped position, the protrusions 170a in the first row of protrusions 170a are received in the longitudinal recess 160 on one side of the second leg 114 and the protrusions 170b are received in the longitudinal recess 160 on the other side of the second leg 114 when the ligation clip 100 is in the clamped position. In some embodiments, each of the protrusions 170a on the first side of the clamping surface 122 is longitudinally offset from each of protrusions 170b positioned on the other side of the clamping surface 128 such that the protrusions 170a and 170b are alternatingly positioned on opposite sides of the clamping surface 122 along the length of the clamping surface 122.

Each of the protrusions 170a, 170b has a triangular shape and includes an apex 172 and an angled inner side wall 174. The apex 172 is positioned in opposition to the flat base wall 161a defining the longitudinal recess 160 on the second leg 114 when the ligation clip 100 is in the clamped position (FIG. 15.) The angled inner side wall 174 of each of the protrusions 170a, 170b is positioned in opposition to side walls 161b defining the longitudinal recesses 160 when the ligation clip 100 is in the clamped position (FIG. 15).

Figure 17:
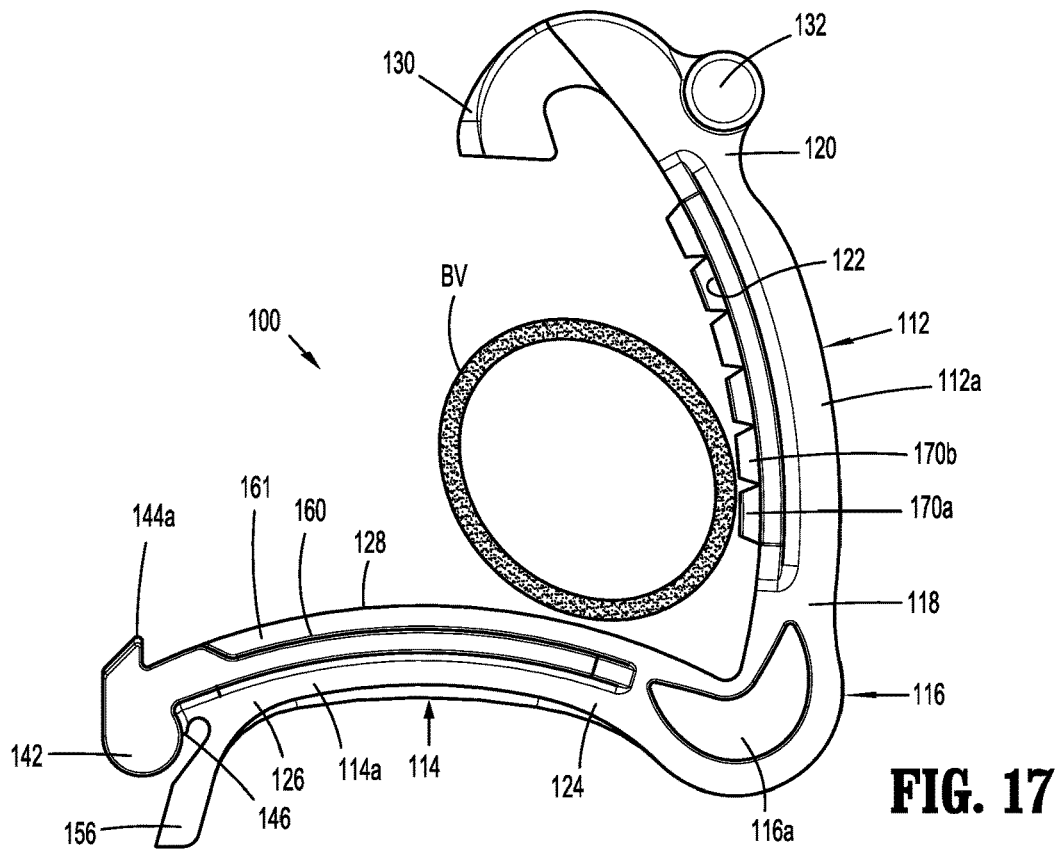
FIG. 17 is a side view of the ligation clip shown in FIG. 13 positioned about body tissue in an open position.
Figure 18:
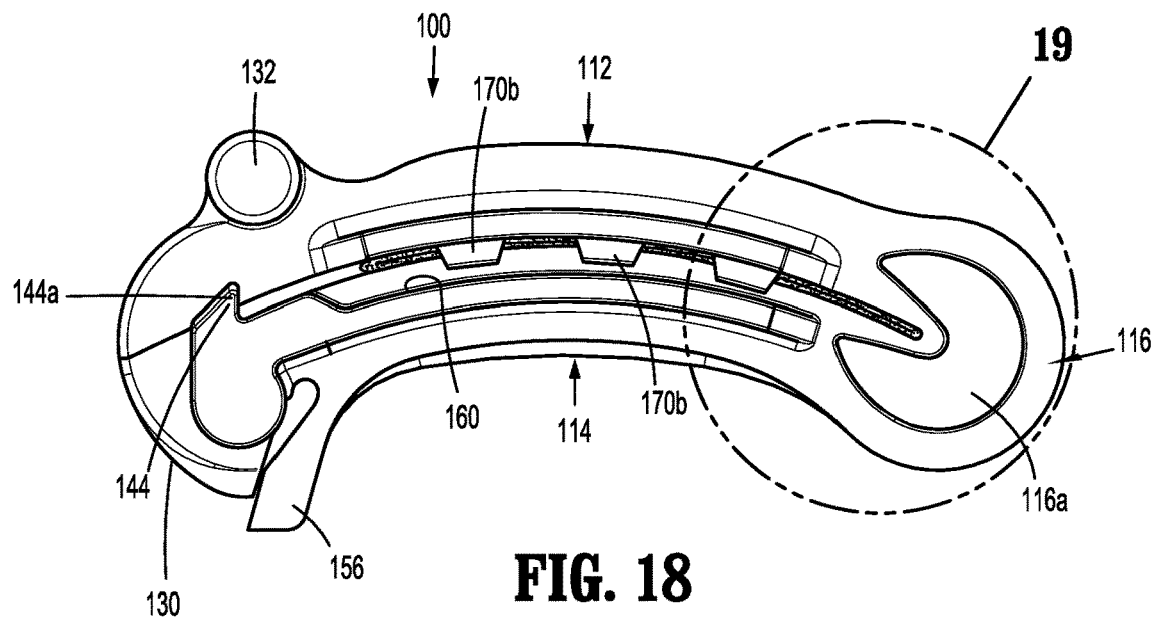
FIG. 18 is a side view of the ligation clip shown in FIG. 17 positioned about the body tissue in a clamped position.
Figure 19:
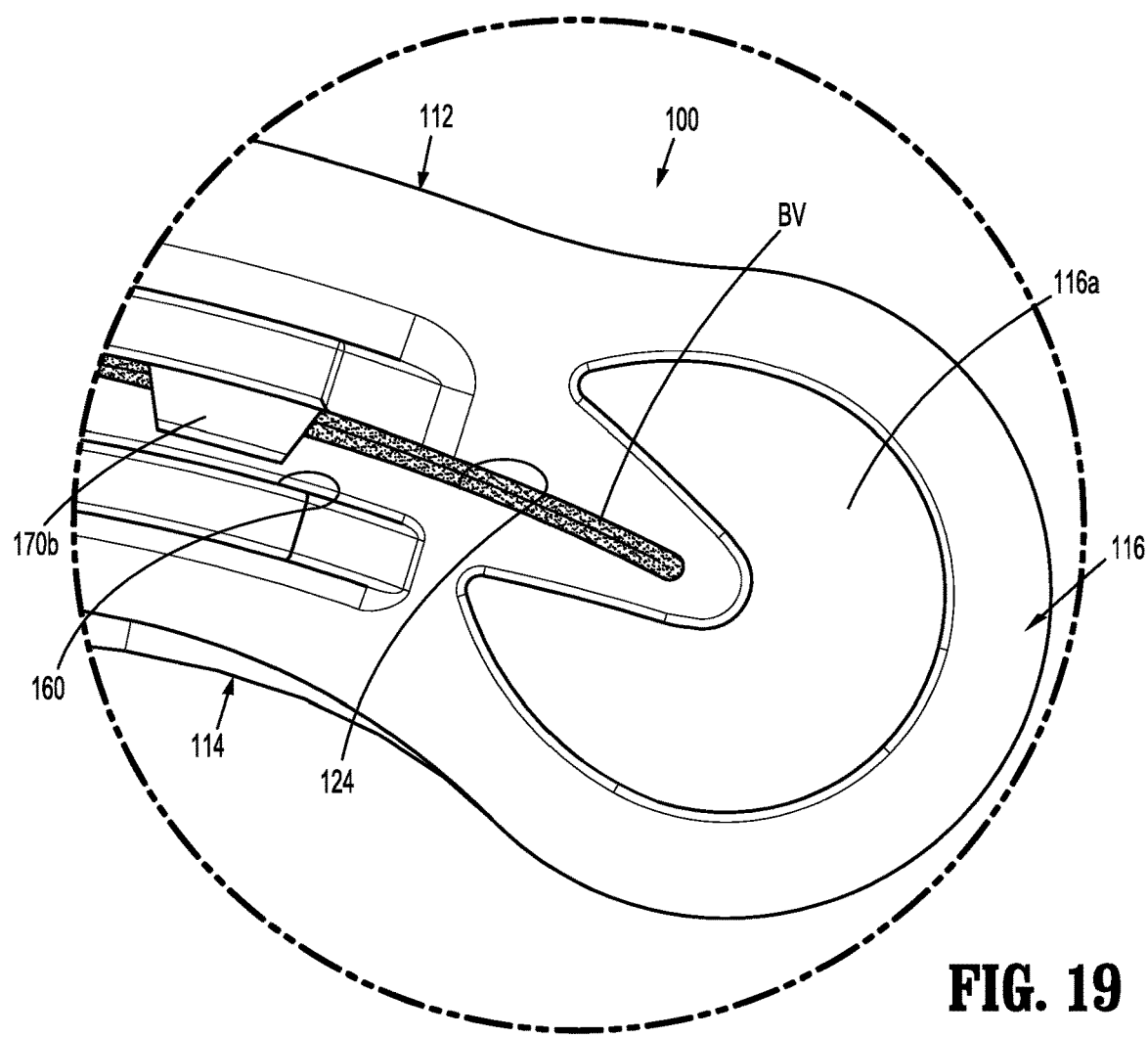
FIG. 19 is an enlarged view of the indicated area of detail shown in FIG. 18.
Figure 20:
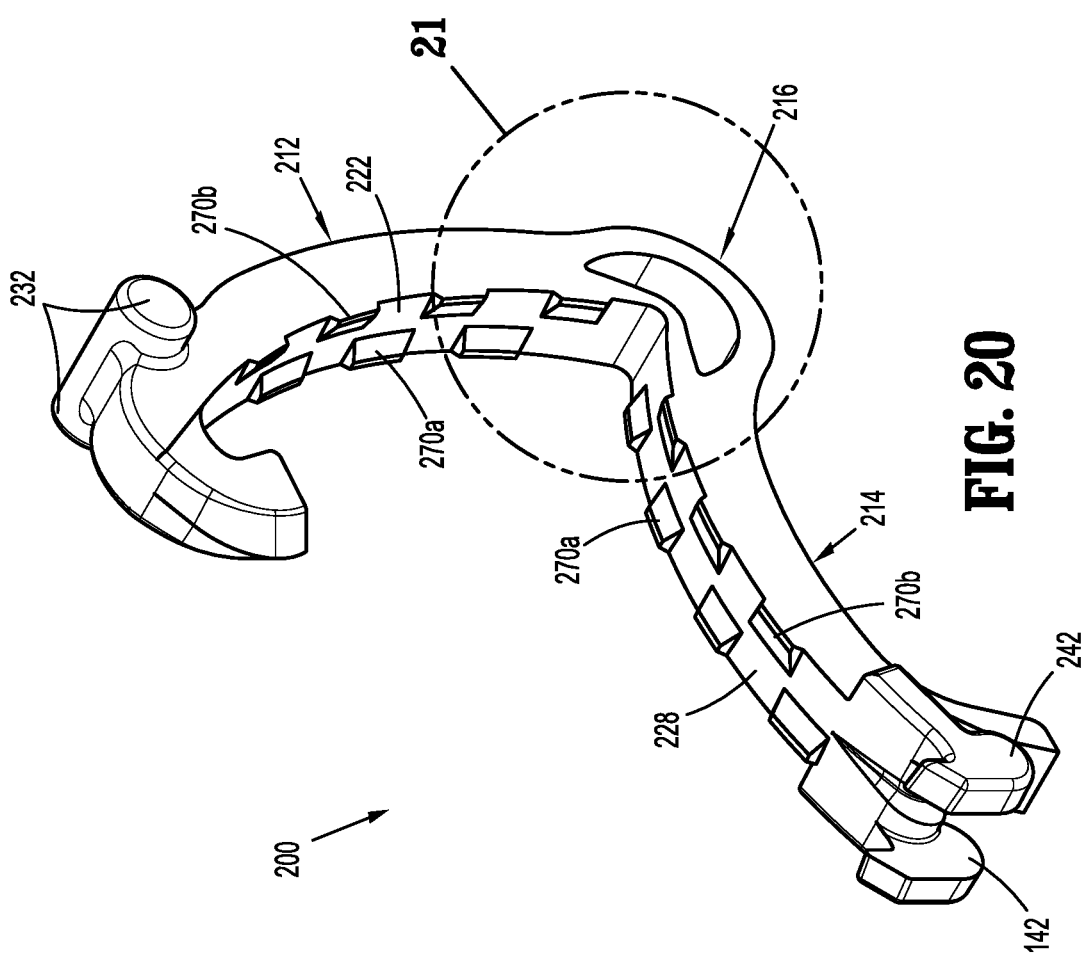
FIG. 20 is a side perspective view of another exemplary embodiment of the presently disclosed ligation clip in an open position.

Referring to FIGS. 17-19, in use, the ligation clip 100 is supported on the end effector 16 of the clip applier 10 (FIG. 1) by positioning the first and second legs 112, 114 of the ligation clip 100 within the slots 72 (FIG. 4) of the first and second jaws 42, 44 of the clip applier (FIG. 3) such that the bosses 132, 142 of the first and second legs 112, 114 of the ligation clip 100 are received in the cutouts 74 (FIG. 3) of the clip applier 10 (FIG. 1). Once the ligation clip 100 is supported on the end effector 16 of the clip applier 10 (FIG. 9), the procedure described above in regard to the application of the ligation clip 80 can be followed to secure the ligation clip 100 to a body vessel "BV" (FIG. 12). When the ligation clip 100 is clamped about the body vessel "BV" (FIG. 12), the body vessel "BV" is compressed between the clamping surfaces 122,128 of the first and second jaws 112, 114 respectively. In addition, the tissue "BV" is also clamped between the angled inner side walls 174 of the protrusions 170a, 170b and the base wall 161a and the side walls 161 defining the longitudinal recesses 160 of the second jaw 114. The configuration of the protrusions 170a, 170b and their location within the longitudinal recesses 160 minimize movement of the ligation clip 100 on the body vessel "BV" after the ligation clip 100 is in the clamped position (FIG. 18.)

FIGS. 20-28 illustrate another exemplary embodiment of the presently disclosed ligation clip shown generally as ligation clip 200. Ligation clip 200 is similar to ligation clip 100 in most respects and includes a first leg 212, a second leg 214 and a hinge portion 216. The first leg 212 includes a clamping surface 222 that supports first and second rows protrusions 270a, 270b, respectively. The first and second legs 212, 214 support bosses 232, 242, respectively. These features are substantially as described above in regard to the ligation clip 100 and will not be described in further detail herein.

Figure 24:
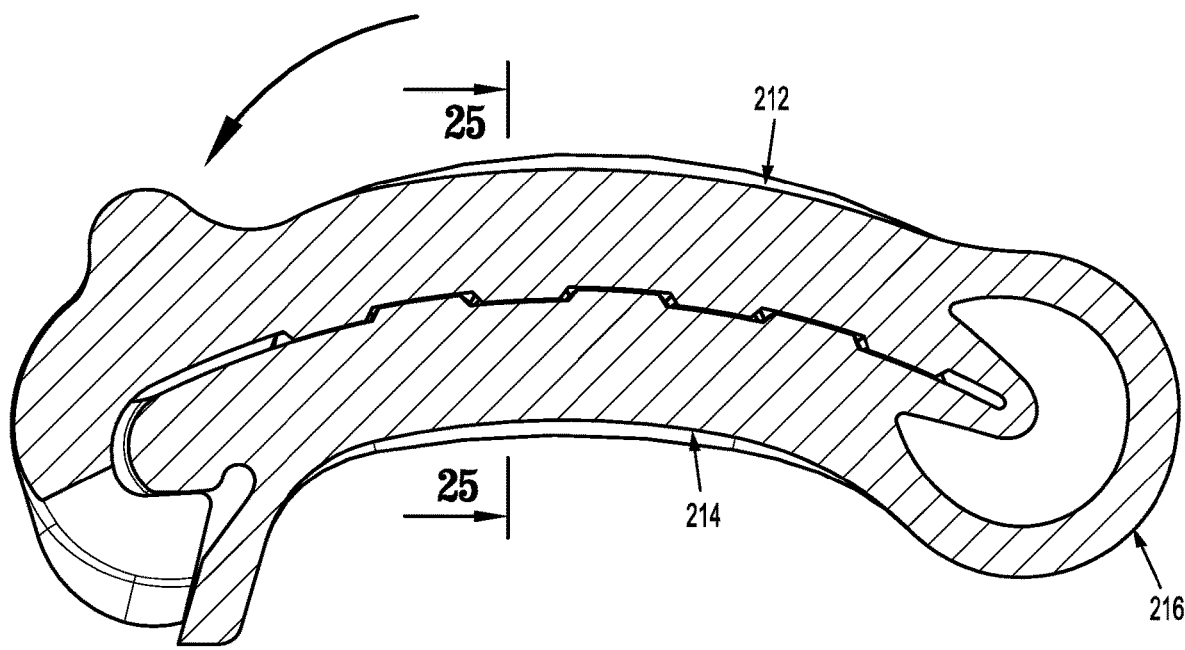
FIG. 24 is a side cross-sectional view of the ligation clip shown in FIG. 22 in a clamped position.
Figure 25:
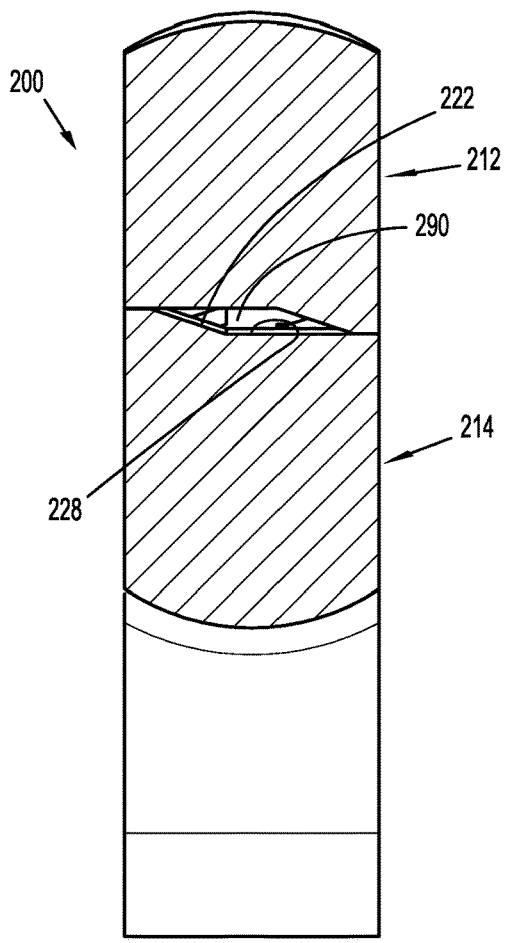
FIG. 25 is a cross-sectional view taken along section line 25-25 of FIG. 24.

In contrast to the ligation clip 100, the second leg 214 of the ligation clip 200 also includes a clamping surface 228 that supports a first row of projections 270a positioned along a first side of the clamping surface 228 and a second row of projections 270b positioned along an opposite side of the clamping surface 228. The first row of projections 270a on the first leg 212 is axially aligned with the first row of protrusions 270a on the second leg 214 when the ligation clip 200 is in a clamped position (FIG. 24). Similarly, the second row of projections 270b on the first leg 212 is axially aligned with the second row of protrusions 270b on the second leg 214 when the ligation clip 200 is in a clamped position (FIG. 24). Each of the first protrusions 270a in the first row of protrusions 270a on the first leg 212 is positioned between adjacent protrusions 270a in the first row of protrusions 270a on the second leg 214 when the ligation clip 200 is in the clamped position. Similarly, each of the second protrusions 270b in the second row of protrusions 27a on the first leg 212 is positioned between adjacent protrusions 270b in the second row of protrusions 270b on the second leg 214.

Figure 21:
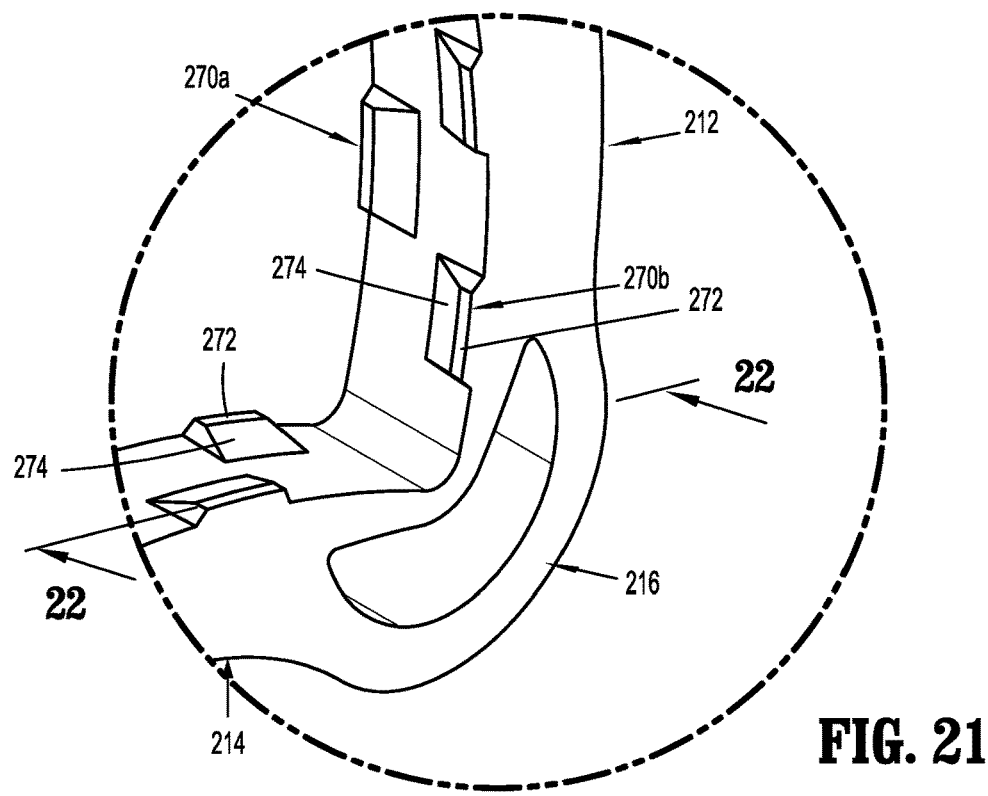
FIG. 21 is an enlarged view of the indicated area of detail shown in FIG. 20.
Figure 22:
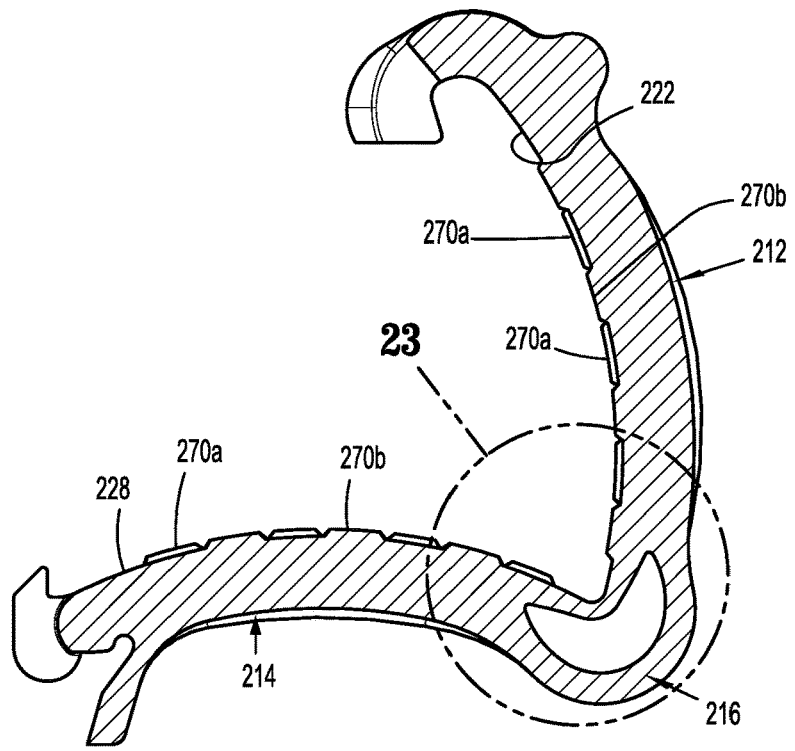
FIG. 22 is a cross-sectional view taken along section line 22-22 of FIG. 21.
Figure 23:
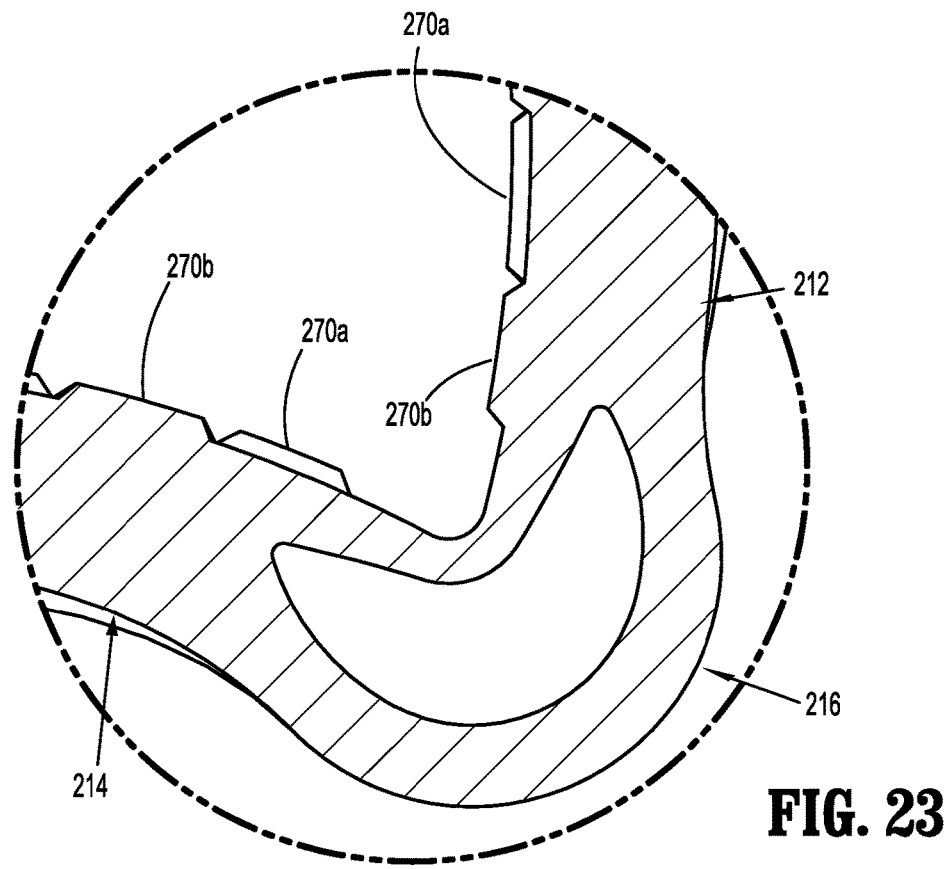
FIG. 23 is an enlarged view of the indicated area of detail shown in FIG. 22.

Each of the protrusions 270a, 270b has an upper flat tissue engaging surface 272 and an angled inner side wall 274 (FIG. 21). The flat tissue engaging surface 272 is positioned in opposition to the opposing leg 212, 214 of the ligation clip 200 when the ligation clip 200 is in the clamped position (FIG. 24.) The angled inner side wall 274 of each of the protrusions 270a, 270b is positioned in opposition to the opposing clamping surface 222, 228 of the opposing jaw 212, 214.

Figure 26:
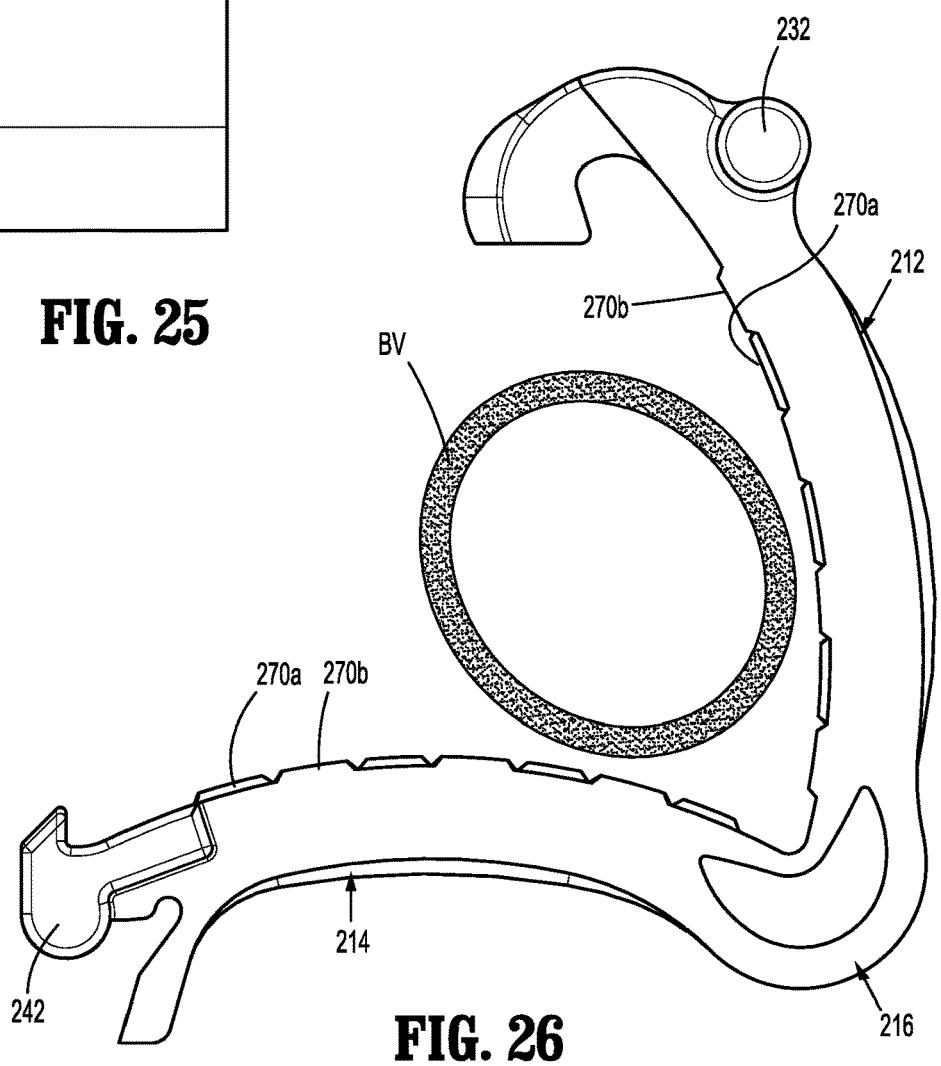
FIG. 26 is a side view of the ligation clip shown in FIG. 20 positioned about body tissue in an open position.
Figure 27:
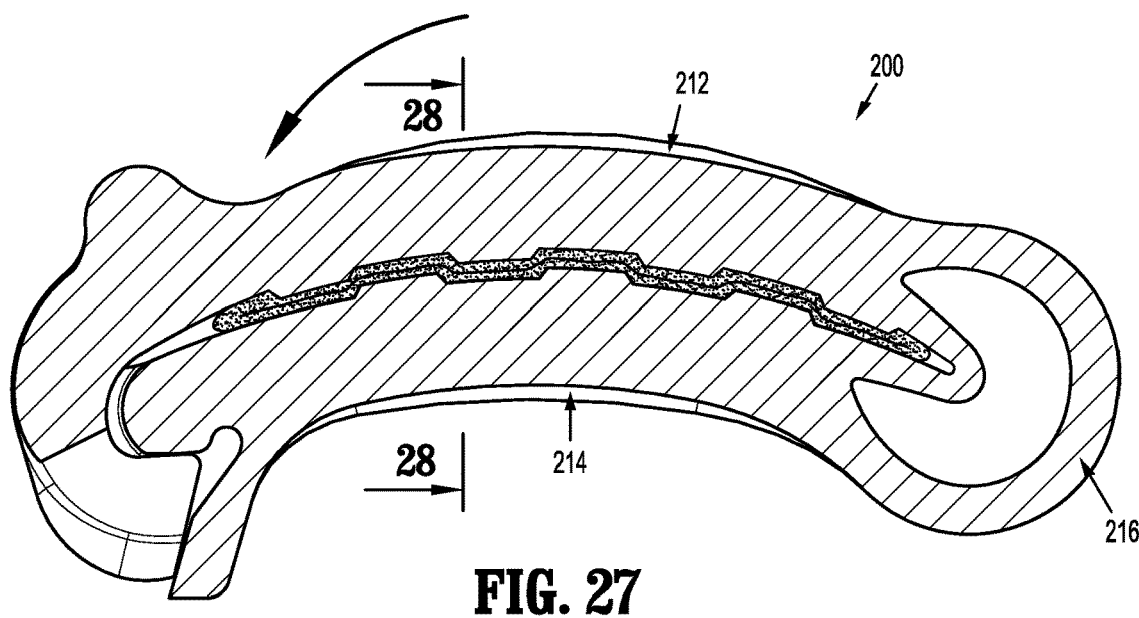
FIG. 27 is a side cross-sectional view of the ligation clip shown in FIG. 26 positioned about body tissue in the clamped position.
Figure 28:
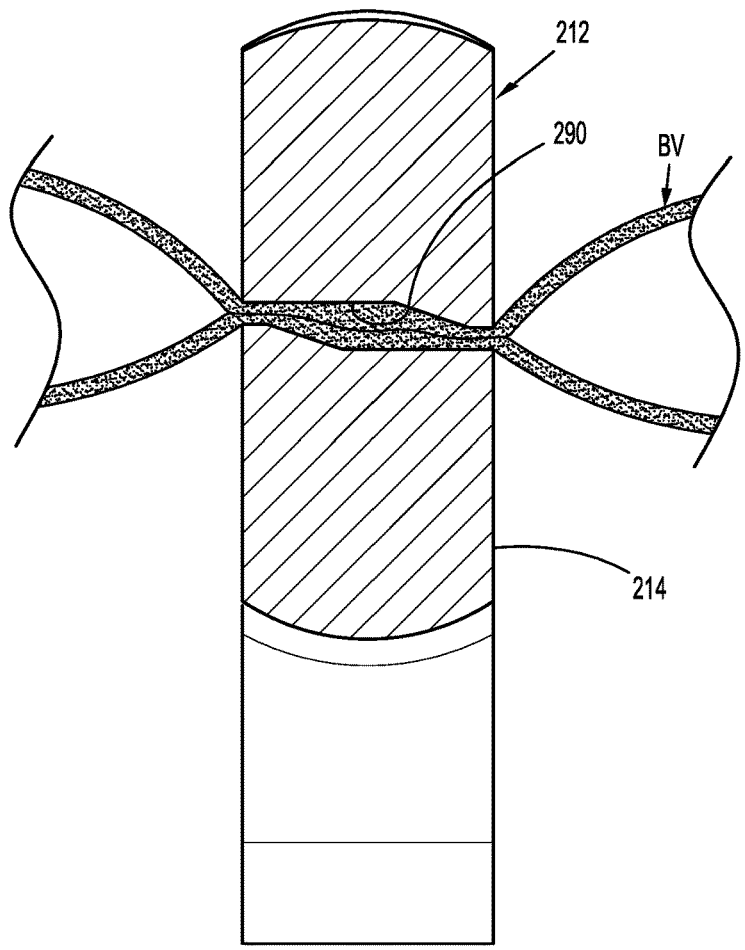
FIG. 28 is a cross-sectional view taken along section line 28-28 of FIG. 27.
Figure 29:
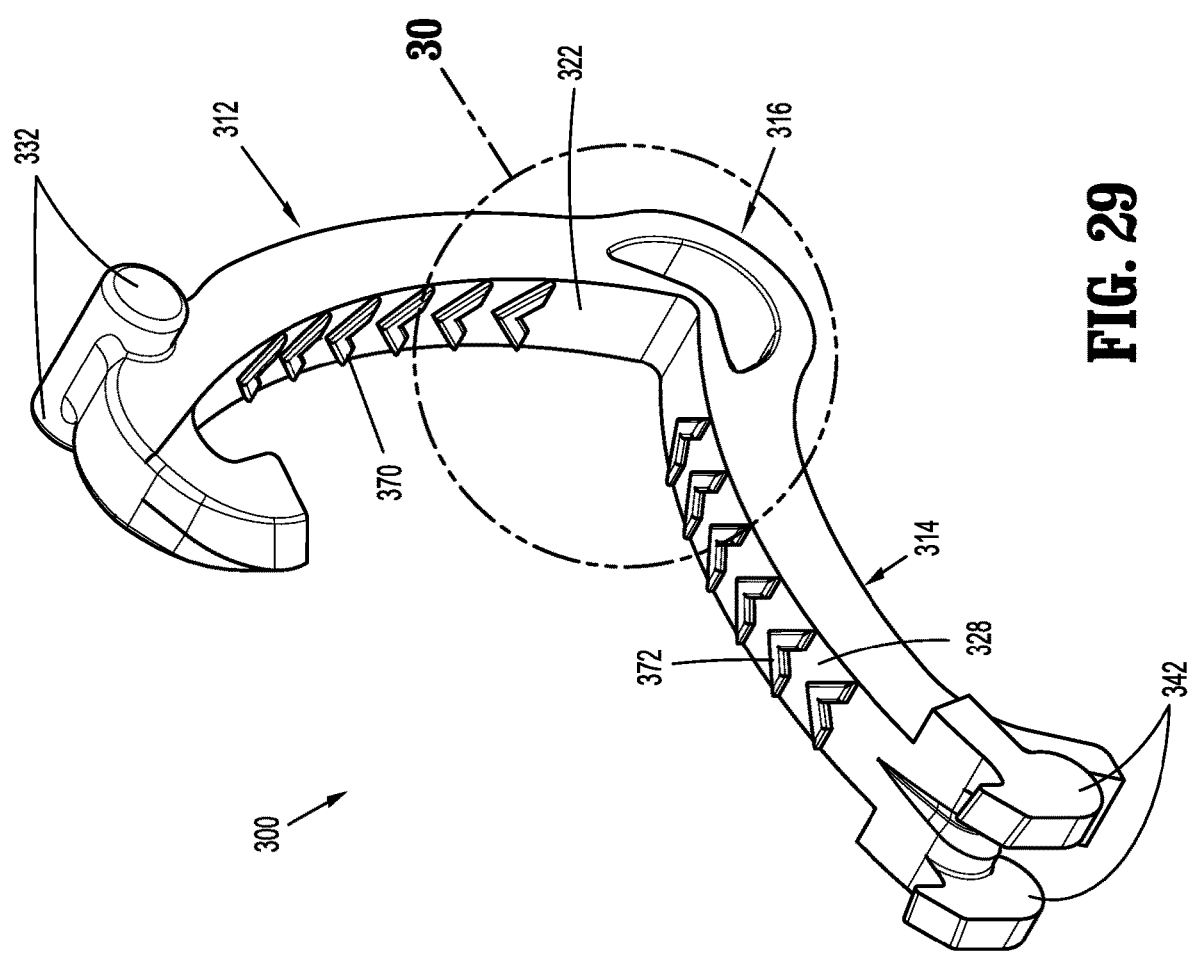
FIG. 29 is a side perspective view of yet another exemplary embodiment of a presently disclosed ligation clip in an open position.
Figure 30:
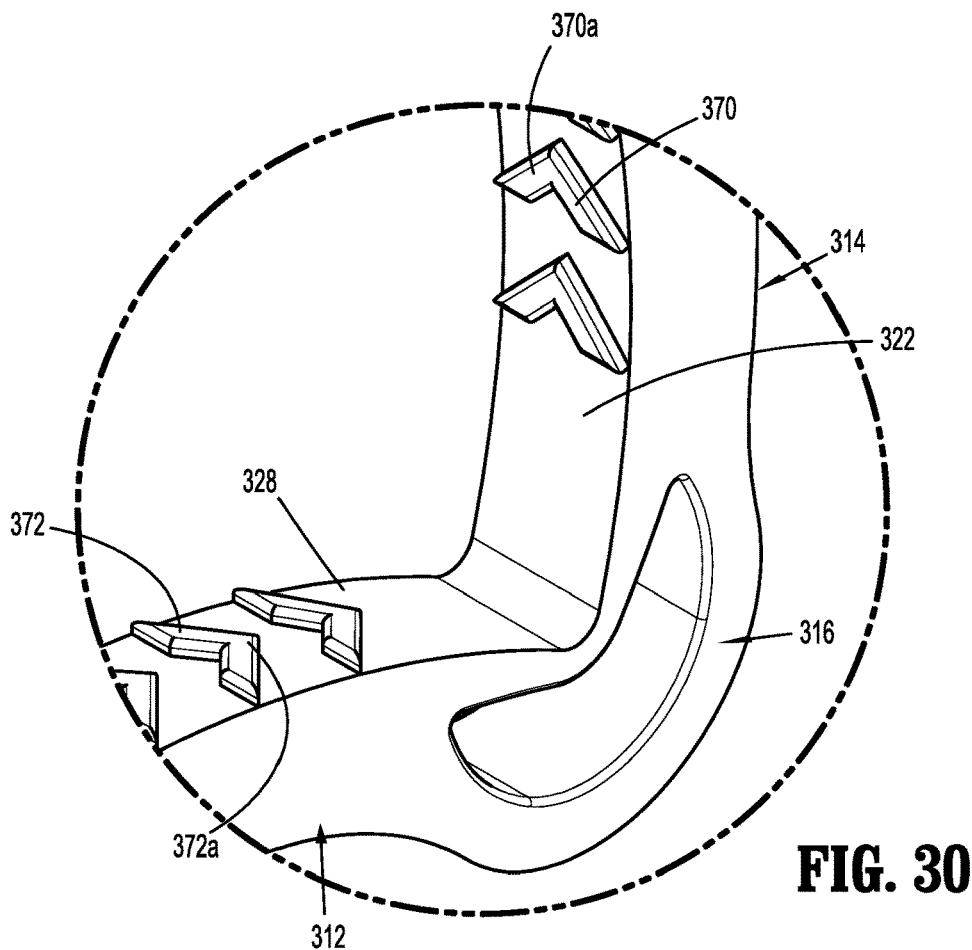
FIG. 30 is an enlarged view of the indicated area of detail shown in FIG. 29.
Figure 31:
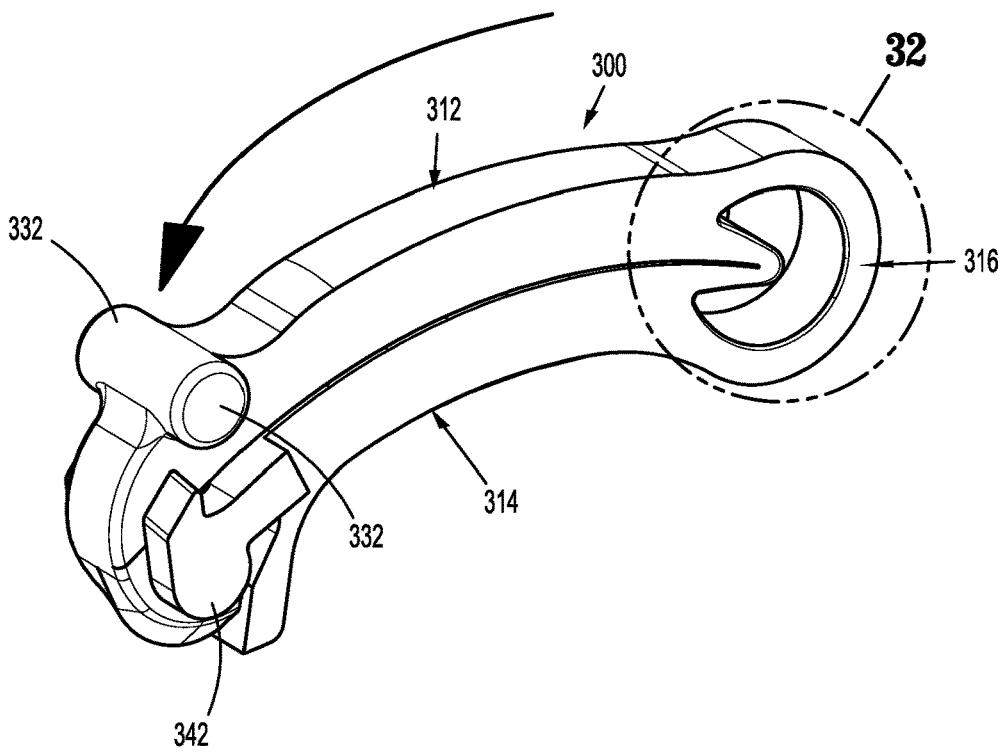
FIG. 31 is a side perspective view of the ligation clip shown in FIG. 29 in a clamped position.
Figure 32:
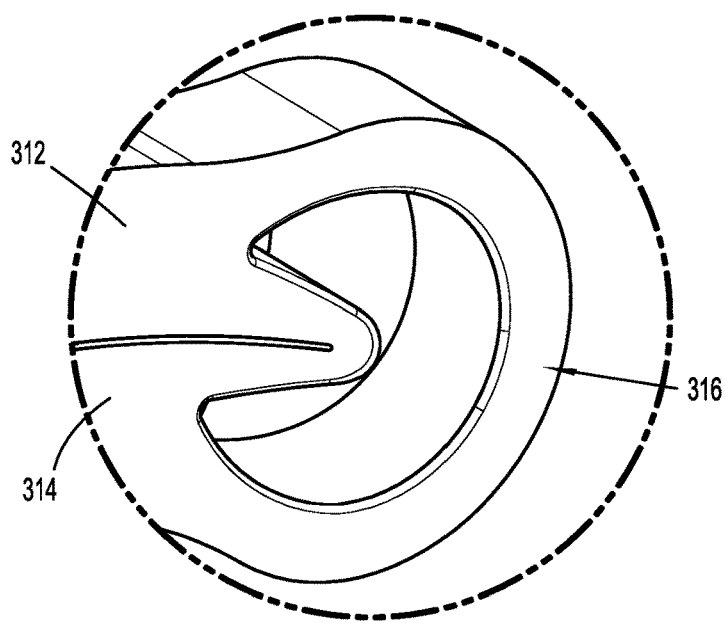
FIG. 32 is an enlarged view of the indicated area of detail shown in FIG. 31.
Figure 33:
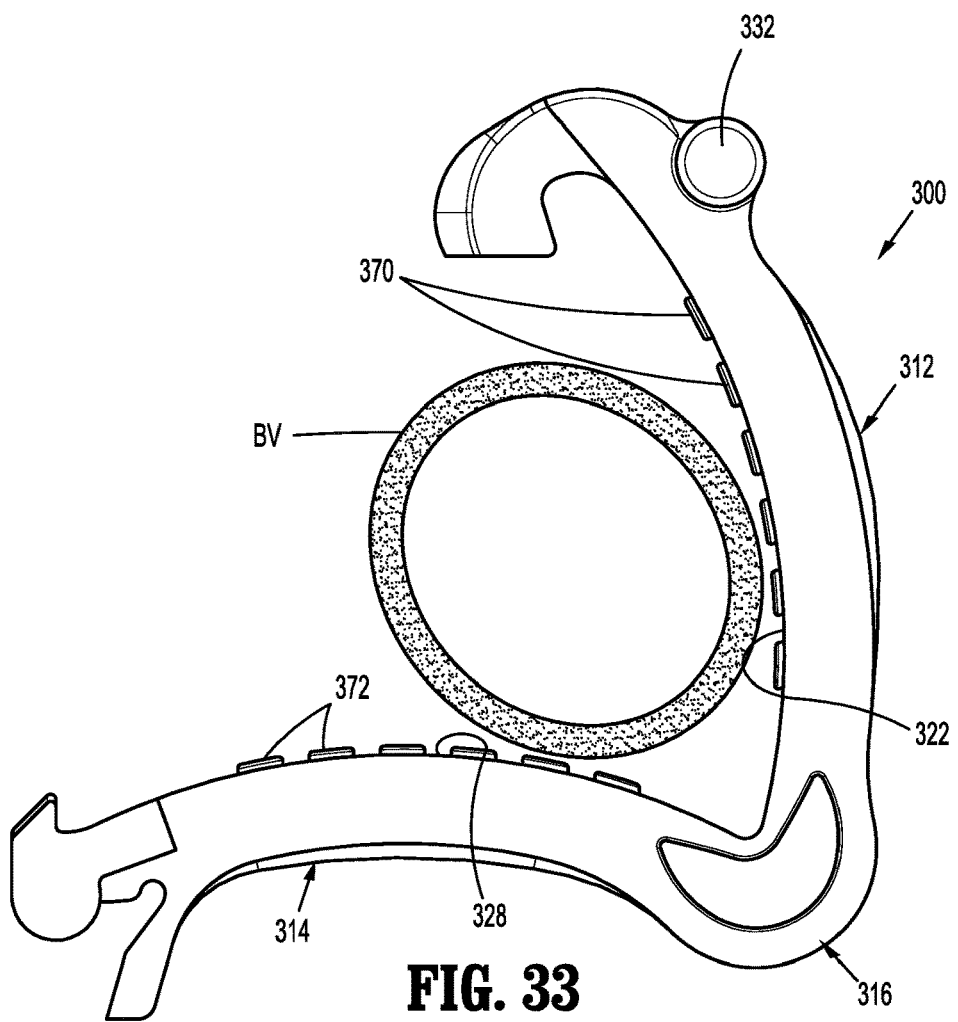
FIG. 33 is a side view of the ligation clip shown in FIG. 29 positioned about body tissue in an open position.
Figure 34:
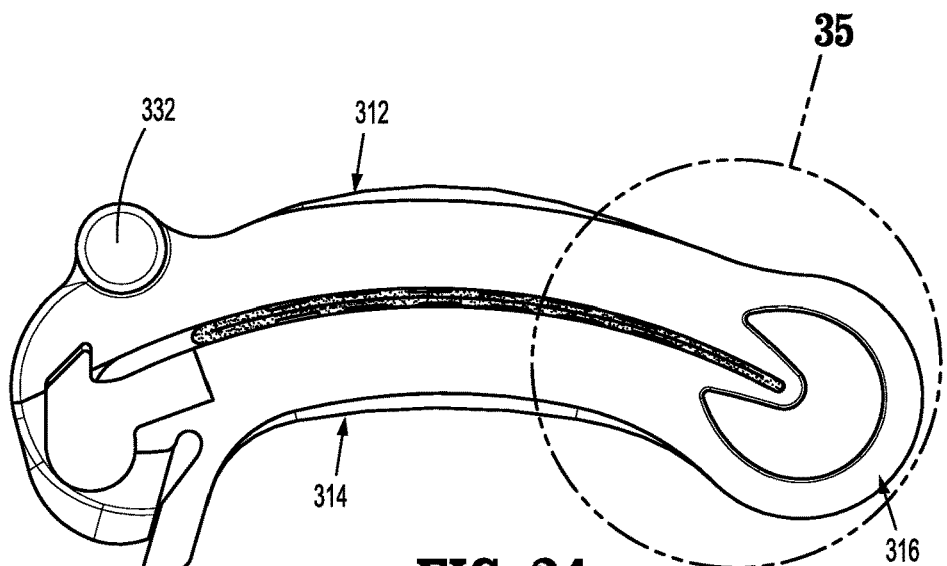
FIG. 34 is a side view of the ligation clip shown in FIG. 33 positioned about the body tissue in a clamped position.
Figure 35:
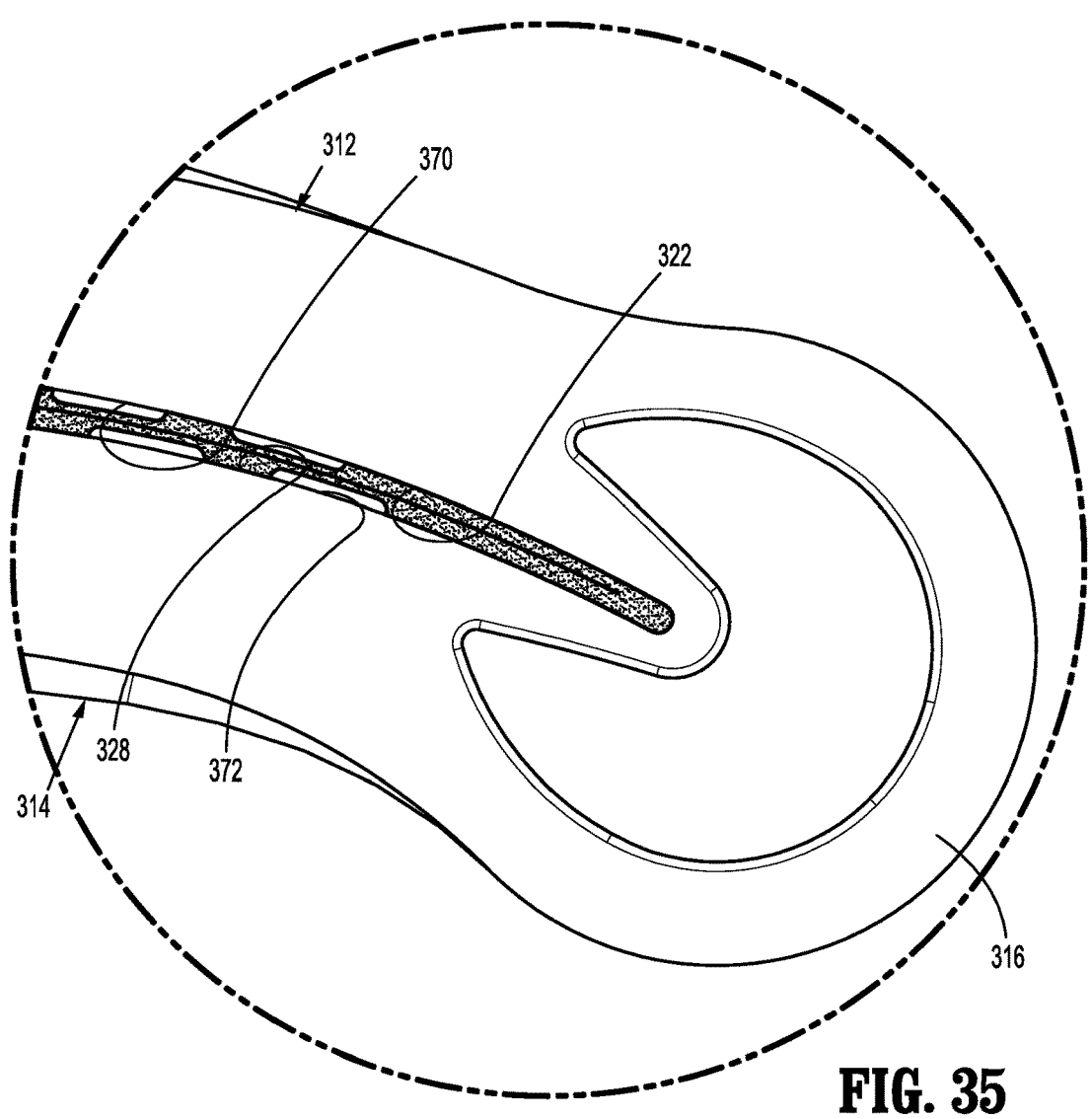
FIG. 35 is an enlarged view of the indicated area of detail shown in FIG. 34.

Referring to FIGS. 26-28, in use, the ligation clip 200 is supported on the end effector 16 of the clip applier 10 (FIG. 1) by positioning the first and second legs 212, 214 of the ligation clip 200 within the slots 72 of the first and second jaws 42, 44 of the clip applier (FIG. 3) such that the bosses 232, 242 of the first and second legs 212, 214 of the ligation clip 200 are received in the cutouts 74 (FIG. 3) of the clip applier 10 (FIG. 1). Once the ligation clip 200 is supported on the end effector 16 of the clip applier 10 (FIG. 9), the procedure described above in regard to the application of the ligation clip 80 can be followed to secure the ligation clip 200 to a body vessel "BV" (FIG. 12). When the ligation clip 200 is clamped about the body vessel "BV" (FIG. 12), the body vessel "BV" is compressed between the clamping surfaces 222, 228 (FIG. 20) of the first and second jaws 212, 214 respectively. In addition, the body vessel "BV" is also clamped between the tissue engaging surface 272 (FIG. 21) and the angled inner side walls 274 (FIG. 21) of the protrusions 270a, 270b and the opposing clamping surface 222, 228 of the first and second jaws 212, 214. The configuration of the protrusions 270a, 270b minimizes movement of the ligation clip 200 on the body vessel "BV" after the ligation clip 200 is in the clamped position (FIG. 18.) In the clamped position of the ligation clip 200, the protrusions 270a, 270b define a recess 290 (FIG. 28) having a shape of a parallelogram wherein the recess 290 includes angled side walls defined by the angled inner side walls 274 of the protrusions 270a, 270b and upper and lower walls that are defined by the clamping surfaces 222, 228.

FIGS. 29-35 illustrate another exemplary embodiment of the presently disclosed ligation clip shown generally as ligation clip 300. Ligation clip 300 is similar to ligation clips 100, 200 in most respects and includes a first leg 312, a second leg 314 and a hinge portion 316. The first leg 312 includes a clamping surface 322 and the second leg 314 includes a clamping surface 328. The first and second legs 312, 314 support bosses 332, 342, respectively. These features are substantially as described above in regard to the ligation clip 100 and will not be described in further detail herein.

In contrast to the ligation clips 100, 200, the first and second legs 312, 314 of the ligation clip 300 include a series of longitudinally aligned chevron-shaped protrusions 370, 372 that are spaced from each other along the clamping surfaces 322, 328 of the first and the second jaws 312, 314, respectively. Each of the protrusions 370 on the first jaw 312 of the ligation clip 300 are positioned between two adjacent protrusions 372 on the clamping surface 328 of the second leg 314 when the ligation clip 300 is in the clamped position. In embodiments, an apex 370a of each of the chevron protrusions 370 on the first jaw 312 point in a distal direction away from the hinge portion 316 and an apex 372a of each of the chevron protrusions 372 on the second jaw 3314 point in a proximal direction towards the hinge portion 316. Alternately, the orientation of the chevron protrusions 370, 372 may both be reversed or individually reversed.

The ligation clip 300 is supported on the clip applier 10 (FIG. 1) in the same manner that the ligation clips 100, 200 are supported on the clip applier 10. As such, the procedure will not be described in further detail herein. When the ligation clip 300 is clamped about tissue, the chevron protrusions 370 on the first jaw 312 compress tissue between the protrusion 370 and the clamping surface 328 of the second jaw 314, and the chevron protrusions 372 on the second jaw 314 compress tissue between the protrusion 372 and the clamping surface 322 of the first jaw 312.

In embodiments, the ligation clips 80, 100, 200, and 300 described above may be made, in whole or in part, of a resilient bioabsorbable and/or biocompatible polymeric material. Examples of suitable bioabsorbable and/or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The clip may also be made of a polymer material or materials in combination with radiolucent metal alloys. Alternately, other materials may be used to form the clip 10 including biocompatible metals, plastics and composites.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A clip applier comprising:
   an outer tube defining a longitudinal axis and a longitudinal bore extending along the longitudinal axis;
   an actuation member having a proximal portion and a distal portion including a cam member, the actuation member being movably positioned within the longitudinal bore of the outer tube between first and second positions; and
   an end effector including a first jaw and a second jaw, each of the first and second jaws being pivotably coupled to the outer tube such that the end effector is movable between open and clamped positions, each of the first and second jaws including a proximal portion defining a cam slot, wherein the cam member of the actuation member is operatively engaged with the cam slots of the first and second jaws such that movement of the actuation member from the first position to the second position moves the end effector from an intermediate position to the open position and subsequently to the clamped position,
   wherein each of the first and second jaws defines a channel and a cutout, the channel of each of the first and second jaws being dimensioned to receive a leg of a ligation clip, and the cutout of each of the first and second jaws is configured to receive a boss of the ligation clip.

2. The clip applier of claim 1, wherein the cam member includes a first protrusion that is received in the cam slot of the first jaw and a second protrusion that is received in the cam slot of the second jaw.

3. The clip applier of claim 2, wherein the cam slots include a proximal portion that extends outwardly away from the longitudinal axis of the outer tube and a distal portion that extends towards the longitudinal axis of the outer tube.

4. The clip applier of claim 1, wherein the outer tube includes a distal portion defining a clevis, the first and second jaws being pivotably secured to the clevis by a pivot member.

5. The clip applier of claim 1, wherein the distance between an outer surface of the first and second jaws in the intermediate position is no greater than the diameter of the outer tube.

6. A method of clamping a ligation clip onto tissue comprising:
   positioning a ligation clip between the first and second jaws of the end effector of the clip applier of claim 1, with the end effector in an intermediate position between an open position and a clamped position; and
   moving the actuation member in a first direction to initially move the first and second jaws of the end effector from the intermediate position to the open position and to subsequently move the end effector from the open position through the intermediate position to the clamped position.

7. The method of claim 6, further including introducing the end effector into a body cavity through a trocar assembly with the end effector in the intermediate position.

8. The method of claim 6, wherein positioning the ligation clip on the end effector includes sliding first and second legs of the ligation clip into the cam slots in the first and second jaws of the end effector to position bosses on the first and second legs of the ligation clip within the cutouts formed in the first and second jaws of the end effector of the clip applier.

9. The method of claim 6, further including moving the actuation member to move the end effector to the open position.

10. The method of claim 9, further including manipulating the clip applier to position the first and second legs of the ligation clip about a body vessel when the end effector is in the open position.

11. The method of claim 10, further including moving the actuator to move the end effector from the open position through the intermediate position and to the clamped position to clamp the ligation clip about the body vessel.

12. The method of claim 11, wherein moving the actuation member includes advancing the actuation member.

13. The method of claim 11, further including withdrawing the end effector from the trocar assembly after the end effector is moved to the clamped position.

* * * * *